US011224480B2

(12) United States Patent
Smith et al.

(10) Patent No.: US 11,224,480 B2
(45) Date of Patent: Jan. 18, 2022

(54) MEDICAL DEVICES AND RELATED METHODS

(71) Applicant: Boston Scientific Scimed, Inc., Maple Grove, MN (US)

(72) Inventors: Paul Smith, Smithfield, RI (US); Aidan McGlinchey, Dallas, TX (US); Allyn Jensrud, Brookline, MA (US); Ramon Estevez, Lowell, MA (US); Mingxiang Xu, Wayland, MA (US); Niklas Andersson, Wayland, MA (US); Gary Jordan, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 588 days.

(21) Appl. No.: 16/111,818

(22) Filed: Aug. 24, 2018

(65) Prior Publication Data
US 2020/0060756 A1   Feb. 27, 2020

(51) Int. Cl.
*A61B 18/14*   (2006.01)
*A61M 25/00*   (2006.01)

(52) U.S. Cl.
CPC ..... *A61B 18/1492* (2013.01); *A61M 25/0082* (2013.01); *A61B 2218/002* (2013.01); *A61M 2205/054* (2013.01)

(58) Field of Classification Search
CPC ............... A61B 18/1492; A61B 18/14; A61B 2218/002; A61B 17/320016; A61B 2018/0016; A61B 2018/00577; A61M 25/0082; A61M 2205/054
See application file for complete search history.

(56) References Cited

U.S. PATENT DOCUMENTS

| 4,781,175 A | * | 11/1988 | McGreevy | ........... | A61B 18/042 219/121.5 |
| 4,919,129 A | * | 4/1990 | Weber, Jr. | .......... | A61B 18/1402 604/35 |
| 6,592,580 B1 | * | 7/2003 | Stockert | ............ | A61B 18/1492 606/41 |

(Continued)

FOREIGN PATENT DOCUMENTS

| DE | 102015106749 | 11/2016 |
| EP | 2842509 | 3/2015 |

(Continued)

OTHER PUBLICATIONS

International Search Report and Written Opinion issued in International Application No. PCT/US2018/047928, dated May 16, 2019 (13 pages).

(Continued)

*Primary Examiner* — Linda C Dvorak
*Assistant Examiner* — Annabeth E Rodriguez
(74) *Attorney, Agent, or Firm* — Bookoff McAndrews, PLLC

(57) ABSTRACT

A medical device includes a shaft including a lumen configured to direct a flow of fluid through the shaft and an electrode. A proximal end of the electrode and a distal end of the shaft form a coupling configured to releasably couple the proximal end of the electrode with the distal end of the shaft. When the proximal end of the electrode is coupled to the distal end of the shaft, fluid delivered through the lumen is emitted from the electrode.

16 Claims, 13 Drawing Sheets

(56) References Cited

U.S. PATENT DOCUMENTS

| | | | | |
|---|---|---|---|---|
| 7,699,843 B2* | 4/2010 | Sutter | ............... | A61B 18/1482 |
| | | | | 606/41 |
| 2008/0004656 A1* | 1/2008 | Livneh | .................. | A61B 17/29 |
| | | | | 606/205 |
| 2014/0257277 A1* | 9/2014 | Woloszko | .............. | A61B 18/14 |
| | | | | 606/41 |
| 2017/0105797 A1 | 4/2017 | Mikkaichi | | |

FOREIGN PATENT DOCUMENTS

| | | |
|---|---|---|
| WO | WO 2008005433 | 1/2008 |
| WO | WO 2017034863 | 3/2017 |

OTHER PUBLICATIONS

Huang et al., R., "Comparison of O-Type HybridKnife to Conventional Knife in Endoscopic Submucosal Dissection for Gastric Mucosal Lesions," Medicine, vol. 95, No. 13, Apr. 2016, pp. 1-6. www.md-journal.com.

\* cited by examiner

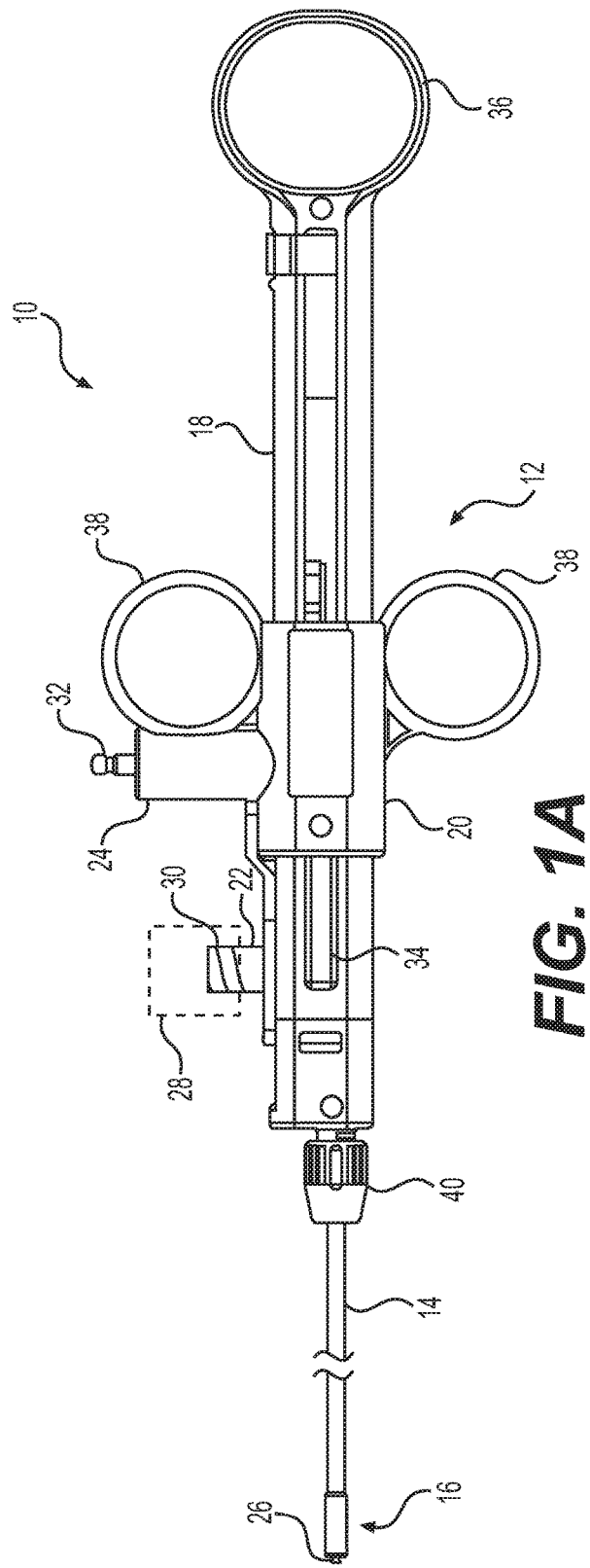
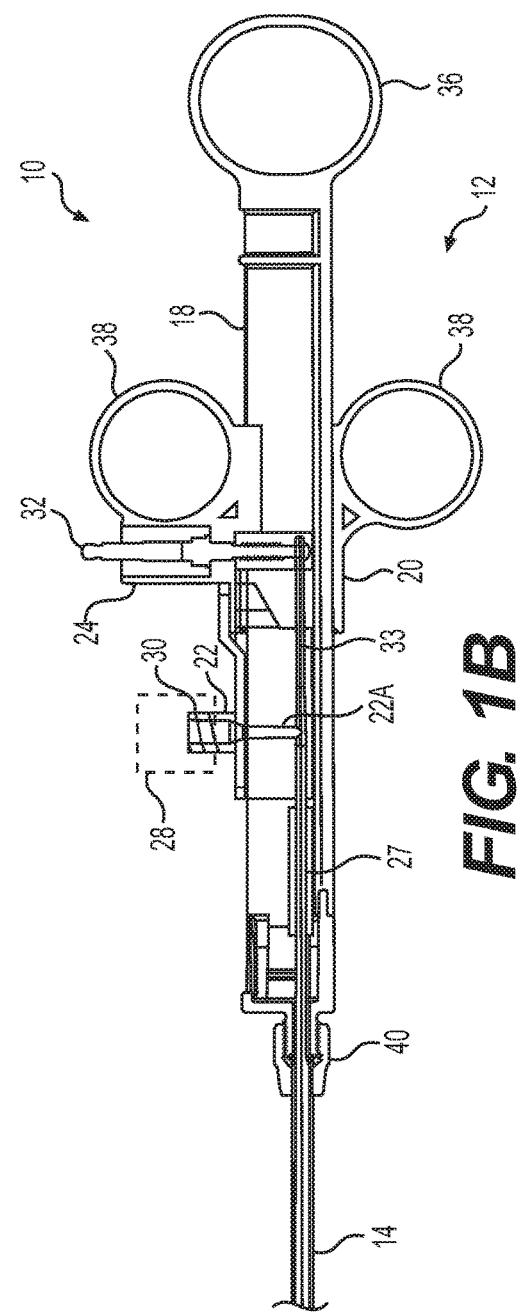

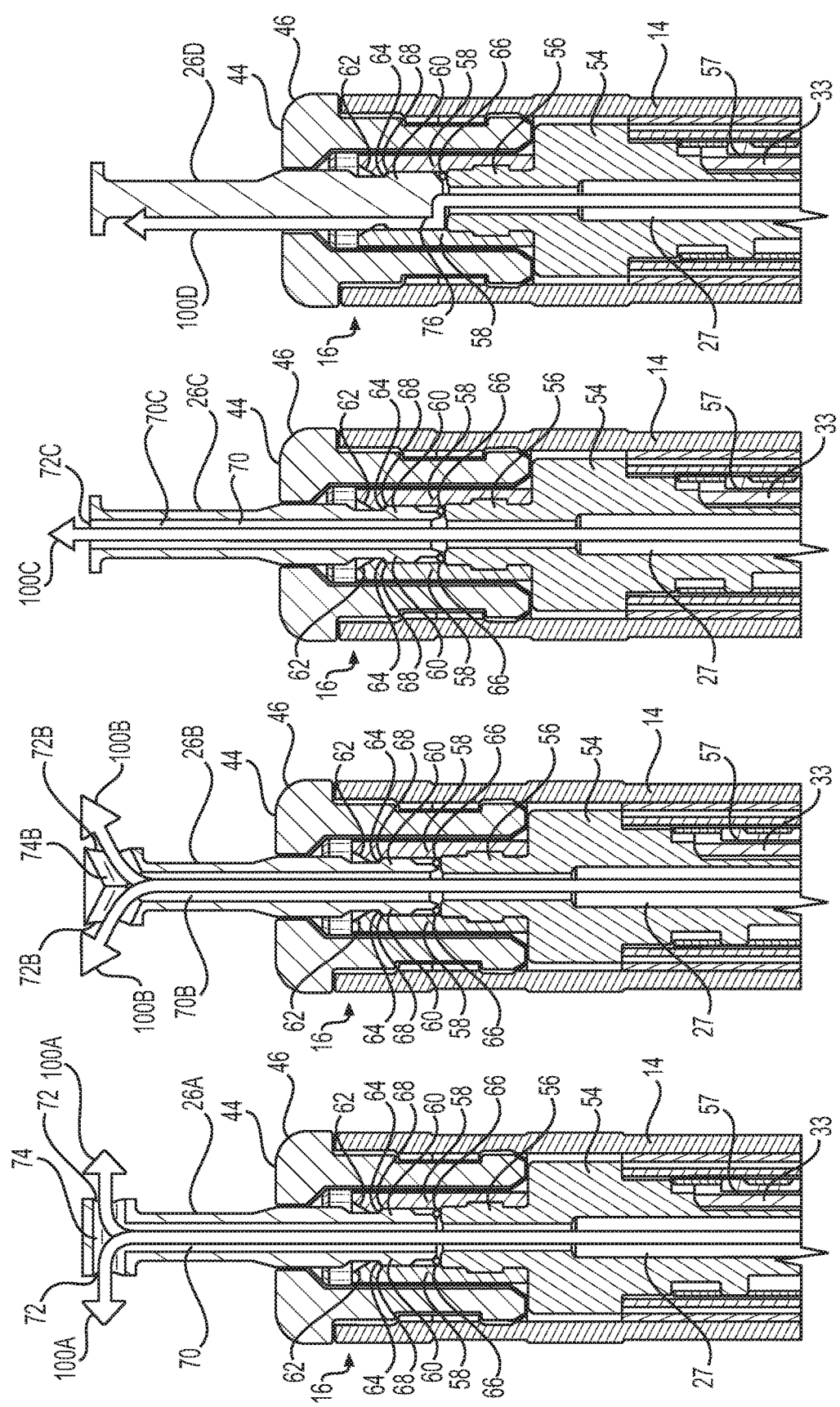

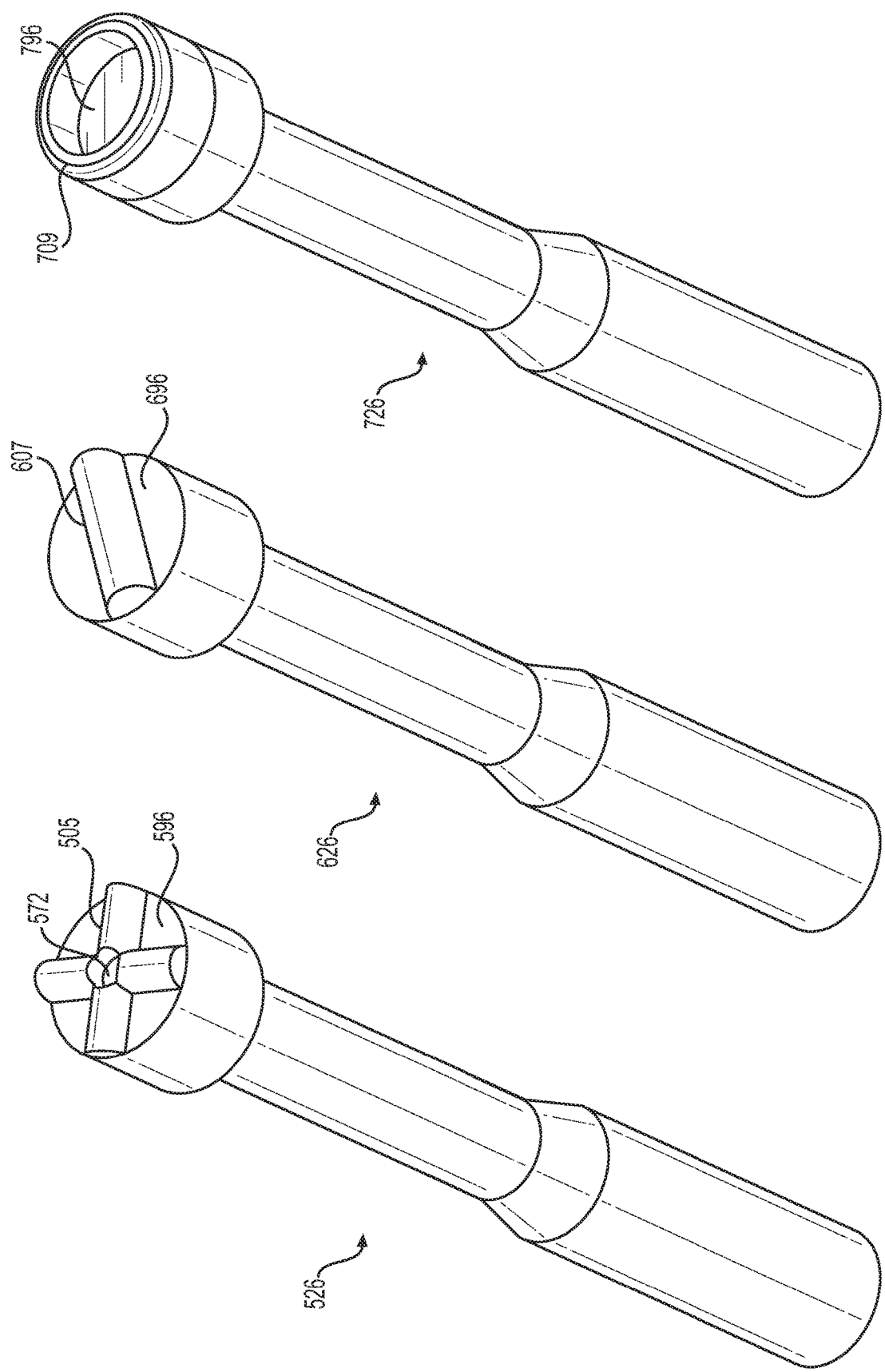

MEDICAL DEVICES AND RELATED METHODS

TECHNICAL FIELD

Aspects of the present disclosure generally relate to medical devices and related methods. In particular, aspects of the present disclosure relate to medical devices and related methods configured for the treatment of tissue by delivering electrical energy to or into tissue, and injecting fluid into and/or under tissue, with one or more electrodes.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle and an energy delivery device for purposes of raising, separating, flushing, cutting, dissecting, ablating, marking, coagulating, cauterizing, or otherwise treating tissue. The injection and energy delivery may be performed separately. For example, in order to deliver energy to the tissue, the user may be required to remove the injection needle from the insertion device and deliver the energy delivery device through the insertion device to the tissue being targeted, and vice versa. During the procedure, the user may alternate using the injection needle and the energy delivery device, and exchange of devices may increase the duration and risks of the medical procedure. Additionally, instances may arise where the type of injection needle needed may change. Also, in some instances, the type of energy delivery device needed may change. This may further increase the duration of the medical procedure and/or limit the types of procedures that may be performed.

The devices and methods of the current disclosure may rectify some of the deficiencies described above or address other aspects of the prior art.

SUMMARY

Examples of the present disclosure relate to, among other things, medical devices configured for treating tissue by delivering electrical energy to the tissue, and configured for delivering fluid into and/or under the tissue. The devices may involve the use of different electrodes, for example, ones with different fluid flow paths, insulation patterns, and/or other characteristics. The present disclosure also relates to methods of assembling the devices, operating the devices, and/or performing procedures with the devices. Each of the examples disclosed herein may include one or more of the features described in connection with any of the other disclosed examples.

In one example, a medical device may include a shaft including a lumen configured to direct a flow of fluid through the shaft and an electrode. A proximal end of the electrode and a distal end of the shaft may form a coupling configured to releasably couple the proximal end of the electrode with the distal end of the shaft. When the proximal end of the electrode is coupled to the distal end of the shaft, fluid delivered through the lumen may be emitted from the electrode.

The medical device may further include one or more of the following features. The coupling may include one or more arms positioned within the distal end of the shaft. Each of the one or more arms may include a protrusion. Each of the one or more arms may further include at least one of an angled portion at a proximal end of the protrusion and an angled portion at a distal end of the protrusion, and the at least one angled portion may be angled relative to a central longitudinal axis of the distal end of the shaft. The electrode may include one or more receivers configured to receive the one or more arms. The one or more receivers may be radially wider than a portion of the electrode distal to the one or more receivers, and/or than a portion of the electrode proximal to the one or more receivers. The medical device may further include one or more seals configured to form a fluid tight seal between the electrode and the shaft. With the electrode coupled to the one or more arms, the one or more seals may sealingly engage surfaces of the electrode and the shaft to direct fluid from the lumen to the electrode.

The distal end of the shaft may include one or more arms. The one or more arms may be biased to move radially outwardly, and the one or more arms may be longitudinally movable within the distal end. The medical device may further include at least one biasing member configured to bias the arms distally within the distal end of the shaft. The distal end of the shaft may include a central passage with an angled portion that narrows distally. The angled portion may be configured to force the one or more arms radially inwardly as the one or more arms move distally within the distal end of the shaft. The shaft may include a coupling tube with a distal coupling portion configured for securing to the proximal end of the electrode. The distal coupling portion may comprise an elastomeric polymer material configured to couple the coupling tube to the electrode, and to form a seal between coupling tube and the electrode that facilitates fluid flow from the lumen to the electrode. The electrode may include an insulator that only partially covers a distal end face of the electrode. The electrode may include an outlet in the distal end face, and the insulator may include a plurality of protrusions projecting from the distal end face about the outlet. The electrode may include a first conductive member and a second conductive member. The first conductive member and the second conductive member may be electrically separated by an insulating member. The medical device may include a conductor that is longitudinally movable to contact and deliver energy to the first conductive member or to the second conductive member.

In another example, a medical device kit may include a medical device including a handle, and a shaft extending distally from the handle, wherein the shaft includes a lumen. The medical device kit may also include a plurality of electrodes. The shaft may include a distal end having a mechanism therein configured for securing one of the plurality of electrodes to the distal end of the shaft, releasing the one of the electrodes from the distal end of the shaft, and securing another of the electrodes to the distal end of the shaft.

The medical device kit may further include one or more of the following features. At least two of the electrodes may differ in structure, and coupling different electrodes of the plurality of electrodes to the shaft may change a fluid flowpath of the medical device. When one of the at least two electrodes is coupled to the distal end of the shaft, fluid delivered through the central lumen may be delivered through the coupled electrode, movement of a portion of the handle may control movement of the coupled electrode, and electrical energy delivered through the shaft may be delivered to tissue through the coupled electrode. The distal end of the shaft may include one or more arms each including a protrusion, an angled portion proximal to the protrusion, and an angled portion distal to the protrusion. Each of the plurality of electrodes may include a receiver portion that is radially wider than a portion of the electrode distal to the receiver portion and a portion of the electrode proximal to the receiver portion. The protrusion may engage the receiver portion.

In a further example, a method may include coupling a first electrode with a first structure to a distal end of a medical device shaft, and the coupling may include releasably coupling an internal component of the medical device shaft to a portion of the first electrode. The method may further include uncoupling the first electrode from the distal end, and coupling a second electrode with a second structure to the distal end, where the second structure is different than the first structure.

The method may further include one or more of the following features. Uncoupling the first electrode may include an action on a medical device handle coupled to a proximal end of the shaft. The action on the medical device handle may retract one or more arms causing the one or more arms to expand and uncouple the arms from a proximal portion of the first electrode.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 1A illustrates an exemplary medical device, and FIG. 1B illustrates a cross-sectional view of the medical device, according to aspects of this disclosure.

FIGS. 3A-3D illustrate cross-sectional views of various electrodes of the distal portion of the medical device, according to aspects of the present disclosure.

FIGS. 8A-8C illustrate perspective views of other exemplary electrodes, according to further aspects of the present disclosure.

DETAILED DESCRIPTION

Figure 2A:
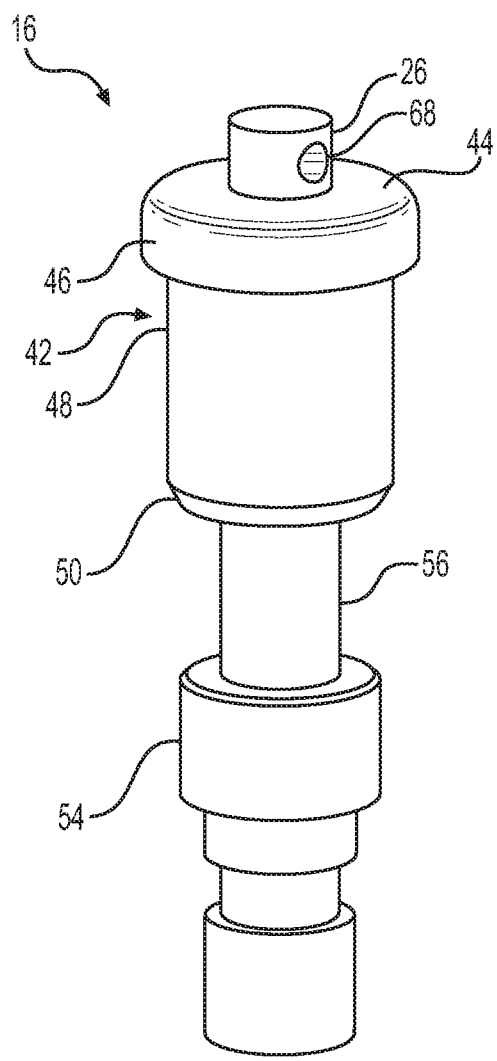
FIGS. 2A and 2B illustrate views of a distal portion of the medical device of FIG. 1A in different operational states, according to aspects of the present disclosure.

Examples of the present disclosure include devices and methods for: facilitating and improving the efficacy, efficiency, and safety of treating tissue when, for example, applying electrical energy to tissue; and delivering fluid into and/or under tissue during a medical procedure. For example, aspects of the present disclosure may provide a user (e.g., physician, medical technician, or other medical service provider) with the ability to apply electrical energy or heat to tissue using a medical device having an electrode, and to deliver fluid into and/or under tissue with the same medical device. Additionally, aspects of the present disclosure may provide the user with the ability to deliver fluid through one or more outlets, with the fluid being diverted on its way to the outlets (e.g., delivered at an angle relative to a central longitudinal axis of the electrode), thereby changing the fluid flowpath. Other aspects of the present disclosure may allow the user to change the electrode to a different electrode, for example, one with a different outlet position and/or arrangement, thereby changing the flowpath of fluid from the medical device. Additional aspects of the present disclosure may allow the user to change the electrode to a different electrode with a different insulation pattern, thereby changing the treatment effect on the treated tissue. Additional aspects of the present disclosure may allow the user to change the electrode to any other electrode having at least one different characteristic, even if, for example, the flowpath and/or insulation pattern is similar. Some aspects of the present disclosure may be used in performing an endoscopic, laparoscopic, arthroscopic, gynoscopic, thoracoscopic, cystoscopic, or other type of procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

FIG. 1 depicts a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an electrode 26. Electrode 26 is electrically connected to hub 24, and may include one or more lumens, passages, recesses, or other surfaces (FIGS. 3A-3D) fluidly connected to, or otherwise in fluid communication with, port 22. Medical device 10 may be inserted into a body lumen of a subject, either through an insertion device (not shown) or alone, such that at least a portion of shaft 14 may be within the subject, while handle 12 may remain outside of the subject. From outside of the subject, a user can manipulate handle 12. Movement of movable body 20 relative to main body 18 in a first direction (e.g., the distal direction) may extend electrode 26 relative to shaft 14 (e.g., move electrode 26 distally relative to a distal end of shaft 14), while movement of movable body 20 relative to main body 18 in a second direction (e.g., the proximal direction) may retract electrode 26 relative to shaft 14 (e.g., move electrode 26 proximally relative to a distal end of shaft 14).

Handle 12 may be coupled to a fluid source via port 22. Port 22 may be in fluid communication with electrode 26 via an internal lumen 27 in shaft 14 (FIG. 1B). Internal lumen 27 may extend longitudinally through main body 18 of handle 12, and port 22 may include a port lumen 22A that extends through port 22 to fluidly connect port 22 to internal lumen 27. Port 22 may be positioned on a distal portion of main body 18. Alternatively, port 22 may be positioned on movable body 20. Moreover, port 22 may include a one-way valve 28, a luer, a seal, threading 30, and/or any appropriate element to maintain a secure connection between handle 12 and the fluid source, minimize or prevent back-flow (e.g., fluid flowing proximally out of port 22), and/or minimize or prevent leakage. In one example, one-way valve 28 may include an outer housing containing an inner elastomeric and/or gelatinous sealing member (not shown).

Handle 12 may be coupled to an energy source through hub 24. Hub 24 may be electrically coupled to electrode 26 via a conductive element 33 in shaft 14. The energy source may be an electrocautery source, a radio frequency generator, a heating source, a current generator, etc. In one aspect, medical device 10 may be used for monopolar electrosurgery, and may include a return electrode positioned remotely from electrode 26 on the subject. In another aspect, medical device 10 may be used for bipolar electrosurgery. In that instance, electrode 26 may include an active electrode portion, and a return electrode may be provided at or near another portion of electrode 26 and/or shaft 14. In one example, two conductive elements may run through shaft 14, where the conductive elements may be electrically isolated from each other, allowing one to conduct energy to the active electrode and the other to conduct energy from a return electrode. Hub 24 may be positioned on movable body 20 and may include one or more pins or prongs 32 to couple to the energy source. Alternatively, hub 24 may be positioned on main body 18.

In one aspect shown in FIG. 1B, prong 32 may extend through hub 24 transverse to a longitudinal axis of handle 12, and may be electrically and physically connected to conductive element 33, such as a wire, a cable, and/or a braided sheath. Conductive element 33 may be electrically conductive or include an electrically conductive element, and conductive element 33 may extend longitudinally through internal lumen 27 and through shaft 14. As shown in FIG. 1B, fluid delivered through port 22 may surround at least a portion of conductive element 33. In another aspect, the energy source may be a part of handle 12 (e.g., an internal battery in handle 12). As alluded to above, a second conductive element (not shown) may be provided as a return pathway where medical device 10 has a bipolar configuration.

As mentioned, handle 12 may control the extension or retraction of electrode 26 relative to the distal end 16 of shaft 14. For example, main body 18 may include a slot 34 and a thumb ring 36. Movable body 20 may be slidably positioned within slot 34 and include one or more finger holes 38. Movable body 20 may be lockable in one or more positions relative to main body 18. Movable body 20 may be coupled to a drive element, and the drive element may impart distal or proximal movement to at least a portion of electrode 26 based on relative movement between main body 18 and movable body 20. In one aspect, conductive element 33 may also act as a drive wire, rod, cable, or the like, such that conductive element 33 imparts distal or proximal movement to at least a portion of electrode 26 while also coupling electrode 26 to hub 24, e.g., the one or more prongs 32, to deliver the energy to (and/or from) electrode 26.

As shown in FIGS. 1A and 1B, shaft 14 extends from a distal portion of main body 18 to distal end 16, and may surround at least a portion of electrode 26. Shaft 14 may be coupled to handle 12 via a coupler 40, which may surround a portion of shaft 14 and screw onto main body 18 to secure the elements. Shaft 14 may be a sheath that surrounds at least a portion of one or more lumens (e.g., lumen 27) and the drive wire (e.g., conductive element 33). In another aspect, shaft 14 may be an extrusion that includes one or more lumens extending from handle 12 to distal end 16.

Figure 2B:
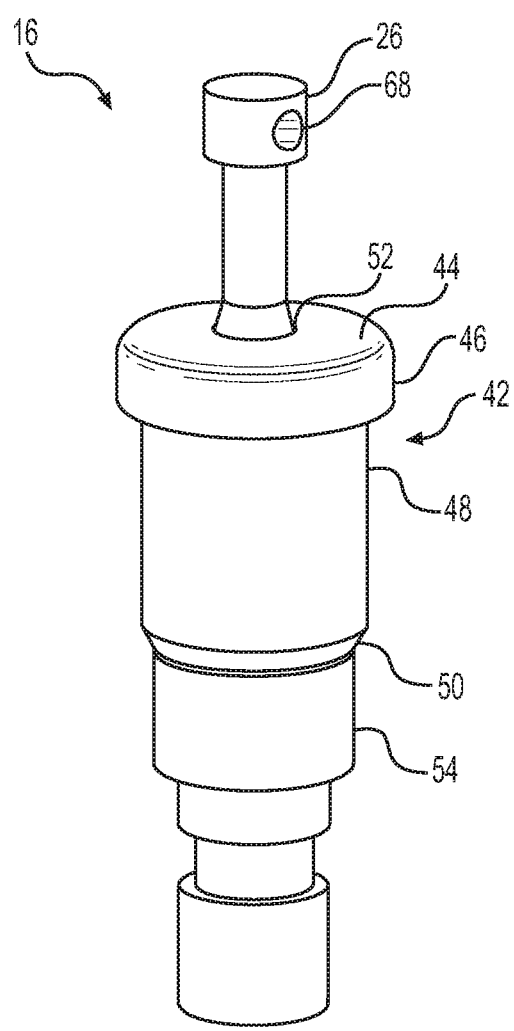

FIGS. 2A and 2B illustrate additional aspects of distal end 16. It is noted that FIGS. 2A and 2B illustrate the internal components of distal end 16, without showing the distal portion of shaft 14 that may radially surround at least a portion of distal end 16. FIGS. 2A and 2B show perspective views of a portion of distal end 16, with a portion of electrode 26 positioned within an end cap 42 of distal end 16. End cap 42 may include a distal end face 44 and graduated surfaces 46, 48, and 50. End cap 42 may be at least partially electrically insulating. For example, end cap 42 may be formed of a ceramic material or another non-conductive material. Alternatively, only distal end face 44 and an internal portion of end cap 42 that contacts and/or surrounds electrode 26 may be electrically insulating. Distal end face 44 includes a central opening 52 (FIG. 2B) through which electrode 26 may extend and retract.

Electrode 26 may be coupled to a proximal support 54 of distal end 16, which includes a cylindrical extension 56. Proximal support 54 may be coupled to a portion of the drive wire (e.g., conductive element 33) via a wire receiving portion 57 (FIGS. 3A-3D). Cylindrical extension 56 may extend distally and may receive at least a portion of electrode 26. As discussed in detail below, electrode 26 and cylindrical extension 56 may be coupled via a snap fit, friction fit, threading, an elastomeric and/or adhesive material, or other suitable coupling. Cylindrical extension 56 may allow for different electrodes 26 to be removably coupled to distal end 16.

Electrode 26 and proximal support 54 may be movable relative to end cap 42 in response to the relative movement of movable body 20 and main body 18 of handle 12. For example, with movable body 20 in a proximal position relative to main body 18, electrode 26 may be substantially retracted within end cap 42 with only a distal portion of electrode 26 extending distally beyond end cap 42 (FIG. 2A). Then, as movable body 20 is translated distally relative to main body 18, electrode 26 and proximal support 54 translate distally relative to end cap 42 such that a greater portion of electrode 26 extends distally beyond end cap 42 through central opening 52 (FIG. 2B).

Alternatively, although not shown in the figures, with movable body 20 in the proximalmost position, electrode 26 may be fully retracted within central opening 52 of end cap 42. It is noted that while central opening 52 is shown in FIG. 2B as being smaller than a portion of electrode 26, this disclosure is not so limited, and central opening 52 and electrode 26 may include various sizes and arrangements. For example, central opening 52 may be wider than electrode 26 such that electrode 26 may be fully retracted within central opening 52. Such a configuration may be advantageous, for example, in versions of medical device 10 in which fluid flows along the outer surface of electrode 26. Alternatively, central opening 52 may be narrower than a distal portion of electrode 26 such that the distal portion of electrode 26 may always remain partially extended from central opening 52.

In one aspect, electrode 26 is releasably coupled to the rest of distal end 16. As shown in FIG. 3A, electrode 26A may be snap-fit to an internal portion of distal end 16. For example, distal end 16 may include one or more fastening portions 58 extending from and/or coupled to cylindrical extension 56. A proximal portion of electrode 26A may include one or more reception portions 60 including, for example, one or more distal widened portions and/or one or more indentations, which may be shaped to receive the one or more fastening portions 58. For instance, each fastening portion 58 may include a distal angled portion 62 and a protrusion 64. As electrode 26A is inserted into the rest of distal end 16, a proximal portion of electrode 26A may contact distal angled portions 62, and relative movement between the two may push fastening portion(s) 58 radially outward, such that the proximal portion of electrode 26A may be releasably received within or between fastening portions 58. Further movement of electrode 26A proximally (and/or the rest of distal end 16 distally) may bring protrusions 64 into engagement with reception portion 60 of electrode 26A, thereby securing electrode 26A. In one example, one or more fastening portions 58 may include one or more cantilevered arms extending distally from an annular base enveloping cylindrical extension 56, such as a single cantilevered arm, a pair of cantilevered arms projecting from opposite sides of the base, or more than two cantilevered arms projecting from any suitable location on the base. Alternatively, one or more fastening portions 58 may include a compliant sheath enveloping cylindrical extension 56, the sheath having a distal rim portion with distal angled portions 62. It also is contemplated that one or more fastening portions 58 may be integrally formed with proximal support 54.

Distal end 16 includes one or more seals 66 to help ensure that fluid delivered through lumen 27 is directed through electrode 26A. In one aspect, distal end 16 may include a compressible and/or expandable seal 66. For example, seal 66 may be a circular ring of elastomeric material positioned on a distal end of cylindrical extension 56 such that positioning electrode 26A within the one or more fastening portions 58 ensures that electrode 26A abuts and/or compresses seal 66. As such, fluid delivered via lumen 27 may be delivered through an electrode lumen 70 and out of outlets 72 of electrode 26A. In one aspect, proximal support 54, cylindrical extension 56, and fastening portion 58 are conductive such that electrical energy delivered via conductive element 33 may be delivered to or into tissue via electrode 26A.

As mentioned, electrode 26A is removably coupled to distal end 16. For example, pulling electrode 26A distally relative to the rest of distal end 16, and/or pulling the rest of distal end 16 proximally relative to electrode 26A, may expand fastening portions 58 such that electrode 26A may be removed from distal end 16. For example, fastening portions 58 may include proximal angled portions at location(s) 68, and/or reception portions 60 may include distal angled portions at location(s) 68, which may facilitate the expansion of the one more fastening portions 58. The amount of force required to expand fastening portions 58 may be greater than (e.g., approximately two times greater than) the forces that may be imparted to electrode 26A by tissue or other material within a subject during a medical procedure. As such, fastening portions 58 may help to ensure that electrode 26A is only removed from the rest of distal end 16 by a user or other medical professional when distal end 16 is external to the subject.

Additionally, electrode 26A may be temporarily stored in a delivery cartridge (FIG. 10) before coupling to distal end 16 and/or after uncoupling from distal end 16. For example, the cartridge may surround at least the distal portion of electrode 26A (and may surround an entirety of electrode 26A) and may help the user to handle and/or store electrode 26A, for example, in preparation for coupling electrode 26A to the rest of distal end 16. The cartridge may help the user align electrode 26A with central opening 52 and position electrode 26A within the rest of distal end 16 during coupling. As discussed with respect to FIG. 10 below, the cartridge may also store a plurality of electrodes, which may be the same electrode configuration, or may include different electrode configurations.

FIGS. 3A-3D illustrate various electrodes 26, 26A, 26B, 26C, and 26D that may be coupled to and removed from distal end 16. Electrode 26A includes an electrode lumen 70, two outlets 72, and a channel 74 connecting electrode lumen 70 to outlets 72. As shown in FIG. 3A, when electrode 26A is coupled to distal end 16, one or more fluid paths 100A take a substantially radial flow path out of outlets 72.

Electrode 26B includes an electrode lumen 70B, two outlets 72B, and a channel 74B connecting electrode lumen 70B to outlets 72B (FIG. 3B). Channel 74B may include two angled portions connecting electrode lumen 70B to outlets 72B. When electrode 26B is coupled to distal end 16, one or more fluid paths 100B take a diverted flow path out of outlets 72B, at an acute angle relative to, for example, a central longitudinal axis of distal end 16, shaft 14, cap 42, and/or lumen 70B. Fluid flow path(s) 100B may be angled relative to fluid flow path(s) 100A.

Electrode 26C includes an electrode lumen 70C extending to a single outlet 72C (FIG. 3C). Outlet 72C is substantially aligned with electrode lumen 70C. When electrode 26C is coupled to distal end 16, a fluid path 100C forms a forward flow path out of outlet 72C, substantially aligned with the central longitudinal axis of distal end 16, shaft 14, cap 42, and/or lumen 70C, and/or substantially perpendicular to the distal face of electrode 26C.

Electrode 26D includes at least one side opening, channel, passage, and/or hole 76 (FIG. 3D). Side opening 76 may extend from the proximal portion of electrode 26D. Electrode 26D may not include a central lumen. Electrode 26D may, for example, be solid instead of hollow. With electrode 26D coupled to the rest of distal end 16, side opening 76 may be in fluid communication with lumen 27. A fluid path 100D forms a flow path out of side opening 76 such that fluid delivered through lumen 27 exits distal end 16 at a position proximal to the distal tip of electrode 26D. For example, the fluid may flow along an exterior surface of electrode 26D, via a gap between the exterior surface of electrode 26D and the surface forming opening 52. At least a portion of side opening 76 may be radially inward of the sealing surfaces of seal 66.

As discussed above, electrodes 26A-26D may be releasably coupled to and removed from the rest of distal end 16, such that a user may couple one electrode, for example, electrode 26A, to distal end 16, and may then remove electrode 26A and couple another electrode, for example, electrode 26B, 26C, or 26D to distal end 16. For example, a user may couple electrode 26A to the rest of distal end 16 and deliver distal end 16 to an internal lumen of a subject for a first portion of a procedure, for example, where fluid path 100A and/or the structural features of electrode 26A is/are favorable or beneficial. The user may then remove distal end 16 from the subject, and uncouple electrode 26A from the rest of distal end 16. The user may then couple electrode 26B, 26C, or 26D to the rest of distal end 16, and deliver distal end 16 to the internal lumen of the subject for a second portion of a procedure, for example, where fluid path 100B, 100C, or 100D and/or the structural features of electrode 26B, 26C, or 26D, is/are favorable or beneficial. The swapping of electrodes may be repeated as many times as necessary, allowing the user to modify the fluid flow path and/or electrode structural characteristics while treating tissue.

Figure 4:
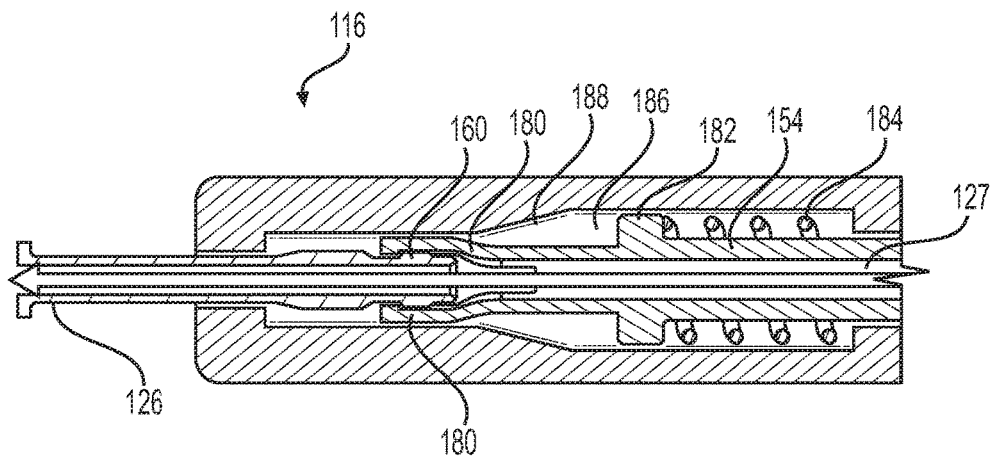
FIG. 4 illustrates a cross-sectional view of an exemplary coupling arrangement configured for releasably coupling electrodes of the distal portion of the medical device, according to aspects of the present disclosure.

FIG. 4 illustrates a cross-sectional view of a ball and socket configuration for coupling and removing electrodes, according to one embodiment of this disclosure. For example, an electrode 126 may include a reception portion 160, and a proximal support 154 within distal end 116 may include fastening arms 180 extending from a radial extension portion 182. Fastening arms 180 may be inherently outwardly biased, such that fastening arms 180 may move radially outward away from each other in the absence of a compressing or constraining force holding them in place. Proximal support 154 may further include a biasing element or spring 184 positioned proximal of radial extension portion 182. Furthermore, distal end 116 may include a central passage 186, and central passage 186 may include an angled widened portion 188. Proximal support 154 may be at least partially moveable longitudinally within central passage 186 between the equilibrium position (as shown) and a retracted position wherein radial extension portion 182 compresses spring 184 and fastening arms 180 expand in angled widened portion 188.

In the retracted position, spring 184 biases radial extension portion 182 distally. As radial extension portion 182 moves distally, angled widened portion 188 forces fastening arms 180 radially inward. As fastening arms 180 move radially inward, fastening arms 180 may engage reception portion 160 of electrode 126. Similarly, a user may retract proximal support 154, for example, via a mechanism on the handle (not shown), such that fastening arms 180 may retract and expand, allowing a user to uncouple electrode 126.

It is noted that, fastening arms 180 may form a circular, or partially circular, socket configured to receive a portion of electrode 126, for example, reception portion 160. Fastening arms 180 may be a plurality of individual arm members spaced apart in the retracted and expanded configuration, or may be a single member that is radially expanded in the retracted and expanded configuration. Additionally, although not shown, the configuration illustrated in FIG. 4 may include one or more seals in distal end 116 to maintain the fluidic connections between lumen 127 and the electrode lumen when electrode 126 is coupled to distal end 116. For example, one or more seals may be positioned radially within fastening arms 180 such that, with electrode 126 coupled to the rest of distal end 116, the seals are positioned between fastening arms 180 and reception portion 160. The one or more seals may be positioned at any one or more positions along the overlap of fastening arms 180 and reception portion 160. Alternatively or additionally, one or more seals may be positioned within distal end 116 distal to angled widened portion 188.

Figure 5A:
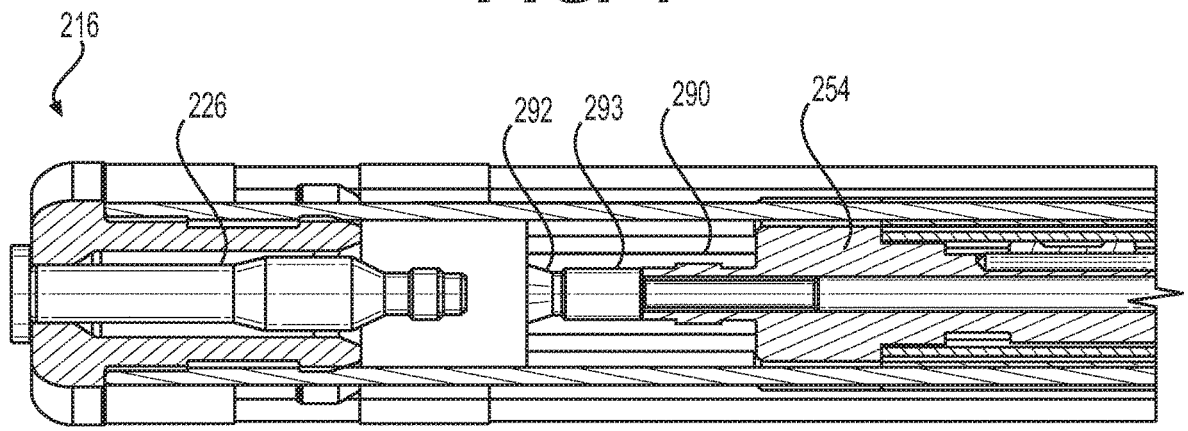
FIGS. 5A and 5B illustrate partially cutaway views of another exemplary coupling arrangement configured for releasably coupling electrodes of the distal portion of the medical device, according to aspects of the present disclosure.
Figure 5B:
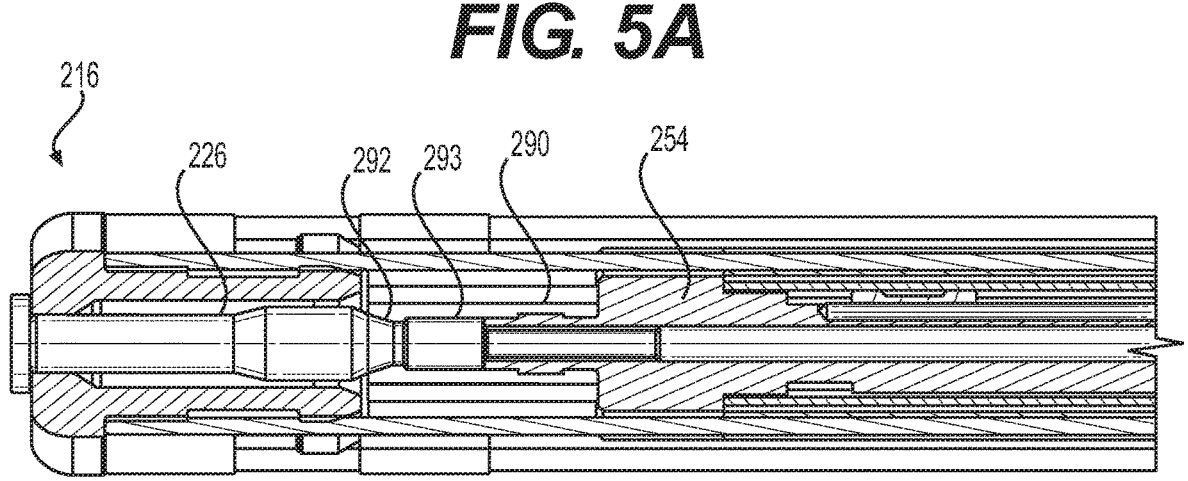

FIGS. 5A and 5B illustrate additional aspects of the disclosure. FIGS. 5A and 5B are partial sectional views of another exemplary mechanism to couple and remove electrodes. For example, a distal end 216 may include a coupling tube 290 that is longitudinally movable with proximal support 254. Coupling tube 290 includes a coupling portion 292 configured to contact the proximal end of electrode 226 and couple electrode 226 to coupling tube 290. Coupling tube 290 may be coupled to a distal end of the fluid lumen and may include an inner lumen 293. Coupling tube 290 may include an elastomeric polymer material that forms or is positioned within coupling portion 292. For example, the elastomeric polymer material may be neoprene, Santoprene™ (thermoplastic vulcanizate), Viton, rubber, etc. Coupling tube 290 may be longitudinally movable between at least a retracted position (FIG. 5A) and an extended position (FIG. 5B). For example, a user may insert electrode 226 into distal end 216 (FIG. 5A), and may extend coupling tube 290 with proximal support 254 from the retracted position to the extended position. Extending coupling tube 290 to the extended position may bring coupling portion 292 into contact with the proximal end of electrode 226. Further extension of coupling tube 290 moves a portion of coupling tube 290 onto and over the proximal portion of electrode 226 such that the proximal portion of electrode 226 is coupled within a portion of inner lumen 293, thus coupling proximal support 254 with electrode 226 (FIG. 5B). Proximal portion of electrode 226 may include one or more contours, for example, a radially narrower portion that widens distally to help in the coupling and/or stretching of coupling tube 290 over the proximal portion of electrode 226. Coupling tube 290 and electrode 226 may securely engage one another in a manner similar to fastening portions 58 and electrodes 26A-26D, and/or similar to fastening arms 180 and electrode 126.

Still further distal movement of coupling tube 290 from the position shown in FIG. 5B may extend electrode 226 distally from the rest of distal end 216. During this movement, coupling tube 290 may extend distally into a lumen or passage in an end cap of distal end 216 (the end cap being similar to cap 42). The wall of coupling tube 290 may be squeezed between the outer surface of electrode 226 and the inner surface of the end cap, thereby enhancing sealing of coupling tube 290 around electrode 226 to facilitate fluid flow through coupling tube 290 into electrode 226.

The elastomeric polymer material within coupling portion 292 may expand around the proximal end of electrode 226 and releasably couple coupling portion 292 to the proximal end of electrode 226. The elastomeric polymer material within coupling portion 292 may also form a seal around the proximal end of electrode 226 such that fluid may be delivered through coupling tube 290 and into electrode 226. Additionally, retracting coupling tube 290 proximally and/or pulling electrode 226 distally may cause the elastomeric polymer material within coupling portion 292 to disconnect from the proximal end of electrode 226, allowing for the user to change electrode 226, as discussed above. Although not shown, it is noted that coupling tube 290 and proximal support 254 may be coupled to a mechanism on the handle in order for a user to extend and/or retract coupling tube 290.

Alternatively or additionally, electrodes 26, 26A, 26B, 26C, 26D, 126, 226, or any other suitable electrodes, may be coupled to the rest of distal end 16 via another form of coupling. For example, any of the electrodes may be screw-fit into the rest of distal end 16 via corresponding (engaging) threading on the proximal portion of electrode 26 and distal portion 56 of proximal support 54. It also is contemplated that any of the electrodes may be coupled to the rest of distal end 16 via a receptacle, and an element to be received (and, in some instances, locked) within the receptacle. For example, the coupling between any of the electrodes and the rest of distal end 16 may include a post, a plug, a pin, a spiral, a lever, a bayonet, etc. on one of the electrode(s) and proximal support 54, and the receptacle may include a ring, an orifice, or another correspondingly shaped connection element on the other of the electrode(s) and proximal support 54. The lockable coupling may further include a detent mechanism, an interference element, and/or a quick connect mechanism. Furthermore, the coupling may include a lever lock, a taper lock, a pin, and/or a keying component, and the coupling may be operably and/or releasably controlled via a mechanism in handle 12.

Other examples of electrodes are described in the paragraphs below. It should be understood that any feature described in connection with electrodes 26, 26A, 26B, 26C, 26D, 126, and/or 226 may be found in any of the other electrodes, and vice-versa. Aspects of the other electrodes also may be shared between them. In particular, any of the examples of electrodes discussed herein may include any of the fluid paths and coupling mechanisms discussed above. Similarly, any of the examples of electrodes discussed herein may include any of the insulation patterns discussed below.

Figure 6B:
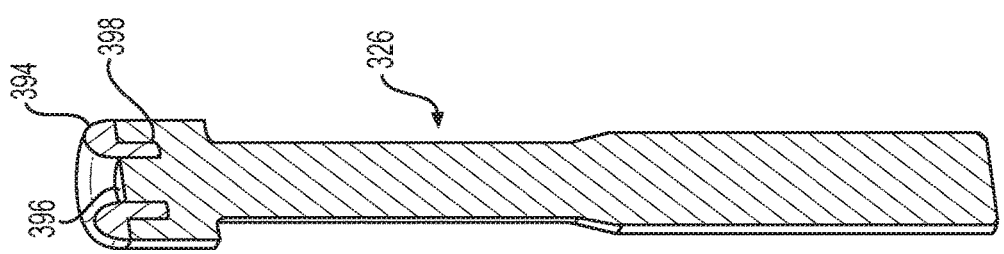
FIGS. 6A and 6B illustrate a perspective view and a cross-sectional view, respectively, of an exemplary electrode, according to aspects of the present disclosure.
Figure 6A:
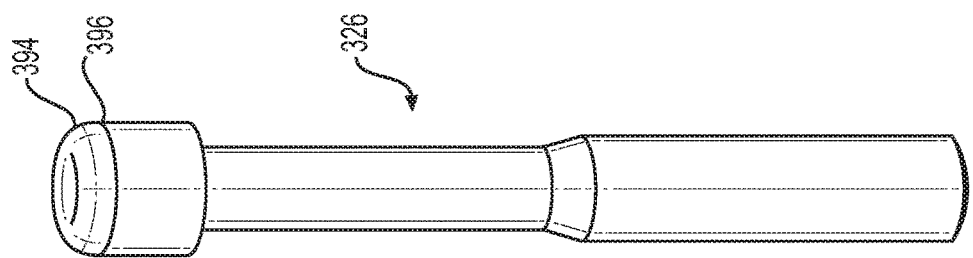

FIGS. 6A and 6B depict perspective and cross-sectional views, respectively, of another electrode 326 that may be positioned and function within medical device 10. Electrode 326 includes an insulator 394, which may form a rounded annular insulation pattern on a distal end face 396 of electrode 326. For example, insulator 394 may be ring or donut shaped, and an outer edge of insulator 394 may be flush with a radially outer edge of electrode 326. As shown in FIG. 6B, electrode 326 may include an annular cavity 398 extending proximally from distal end face 396, and a proximal portion of insulator 394 may be received within cavity 398. Although not illustrated, electrode 326 may include a lumen and one or more outlets as discussed above, to facilitate fluid flow through electrode 326. Alternatively, electrode 326 may be solid as shown, and fluid may flow along its outer surface.

Insulator 394 may provide a buffer or stand off from distal end face 396 and any tissue. In aspect, insulator 394 may abut tissue such that electrode 326 may be energized while insulator 394 helps to insulate the tissue. Additionally, electrode 326 may be advanced further distally and a portion of the abutted tissue may contact the portion of distal end face 396 radially interior of insulator 394 or otherwise not including insulator 394.

Figure 7B:
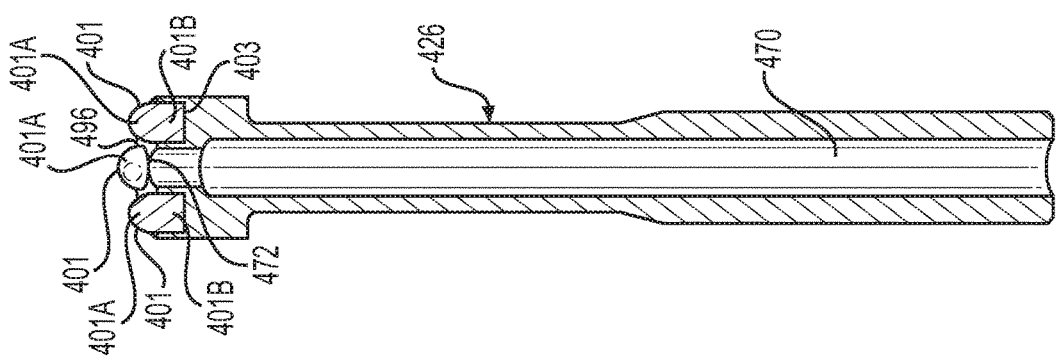
FIGS. 7A and 7B illustrate a perspective view and a cross-sectional view, respectively, of another exemplary electrode, according to aspects of the present disclosure.
Figure 7A:
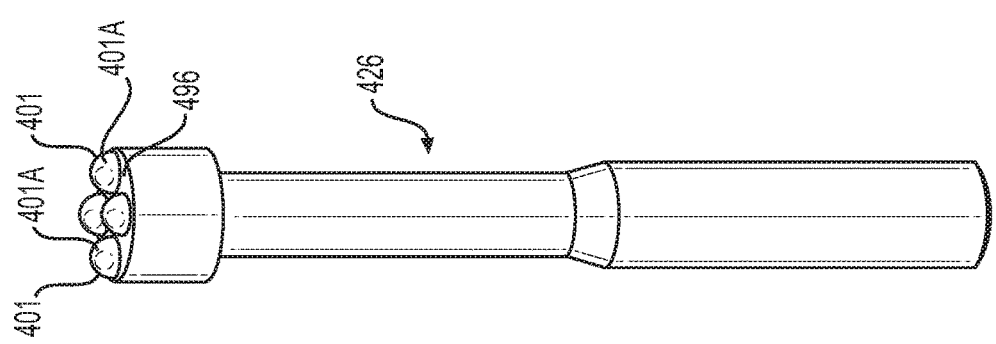

FIGS. 7A and 7B depict perspective and cross-sectional views, respectively, of another electrode 426 that may be positioned and function within medical device 10. Electrode 426 includes an insulator 401, which includes a dotted insulation pattern. Insulator 401 may include substantially hemispherical distal portions 401A and substantially cylindrical proximal portions 401B (FIG. 7B) extending proximally of respective hemispherical distal portions 401A. For example, insulator 401 may include four hemispherical portions 401A positioned on a distal end face 496 of electrode 426. Fewer or more hemispherical distal portions 401A may be used. As shown in FIG. 7B, electrode 426 may include cylindrical cavities 403, and the cylindrical proximal portions 401B of insulator 401 may extend into cylindrical cavities 403. As illustrated, electrode 426 may include a lumen 470 and one or more outlets 472 to deliver fluid, as discussed above. For example, electrode 426 may include a central outlet 472 in distal end face 496, and the hemispherical distal portions 401A of insulator 401 may be positioned radially around outlet 472. Electrode 326 may include a similar flow path for fluid.

FIGS. 8A-8C illustrate additional electrodes 526, 626, and 726. For example, as shown in FIG. 8A, electrode 526 may include a cross-shaped insulator 505 on a distal end face 596. Electrode 526 may include an outlet 572 positioned within cross-shaped insulator 505, or may include one or more outlets as discussed above. Furthermore, cross-shaped insulator 505 may be formed by intersecting semicylindrical insulation portions. Other portions of insulator 505 may be positioned within one or more cavities (not shown) in distal end face 596. Alternatively, cross-shaped insulator 505 may include intersecting polygonal (e.g., rectangular) insulation portions positioned on distal end face 596.

As shown in FIG. 8B, electrode 626 may include a line-shaped insulator 607 on distal end face 696. Line-shaped insulator 607 may bisect distal end face 696 (i.e., with ends of line-shaped insulator 607 positioned 180 degrees apart). Alternatively, line-shaped insulator 607 may be offset and/or not span distal end face 607 (e.g., with ends of line-shaped insulator 607 positioned approximately 150, 120, 90, etc. degrees apart). Although not shown, electrode 626 may include an outlet positioned within line-shaped insulator 607, or may include one or more outlets as discussed above. Furthermore, line-shaped insulator 607 may be formed by a semicylindrical insulation portion. Other portions of insulator 607 may be positioned within one or more cavities (not shown) in distal end face 696. Alternatively, insulator 607 may include a polygonal (e.g., rectangular) insulation portion positioned on distal end face 696.

As shown in FIG. 8C, electrode 726 may include an annular insulator 709 at distal end face 796. Annular insulator 709 may be substantially cylindrical with an open cylindrical middle portion. Annular insulator 709 may include cylindrical inner and outer walls. Annular insulator 709 may include a flat distal portion, and/or may include a rounded radially exterior distal portion on the distal face of annular insulator 709. As shown, the outer wall of annular insulator 709 may be substantially aligned with (flush with) the outer surface of a distal end portion of electrode 726. Annular insulator 709 may extend proximally beyond distal end face 796. For example, electrode 726 may include a narrowed distalmost portion extending proximal of distal end face 796, forming a ledge for annular insulator 709. Annular insulator 709 may be coupled to electrode 726 over the narrowed distalmost portion, with the remainder of the distal portion of electrode 726 being uninsulated. Although not shown, electrode 726 may include an outlet positioned interior to annular insulator 709, or may include one or more outlets as discussed above.

In the aforementioned aspects of this disclosure, the various insulators may be formed by a ceramic, fluoropolymer, polyether ether ketone (PEEK), or other heat resistant and non-conductive material. The insulators provide one or more standoffs of material raised from the distal end face of the electrode. The various electrodes allows for a device that may be used to both cut tissue and mark around an area of tissue. The various electrodes also allow the device to provide hemostasis to control small bleeds. Such electrodes include insulated portions that allow for at least a portion of the distal end face to be exposed to contact tissue. The insulated portions help to minimize the risk of thermal damage and perforation of the tissue by still allowing for the electrode to perform marking and providing hemostasis.

The various electrodes discussed herein are capable of modifying physical properties of tissue when in contact with tissue by delivering energy (e.g., radio frequency energy). The energy delivered may be monopolar or bipolar energy. The various electrodes may be coupled to a shaft, with the shaft configured to extend into a body lumen or cavity of a subject. The shaft includes an electrical element traversing the shaft and connecting the electrode to an energy source, for example, in the handle or coupled to the handle.

The electrodes discussed above include at least two distinct portions: (1) a cutting shaft with a primary axis that is coincident or parallel to a longitudinal axis of the shaft, and (2) a distal portion that includes a cross-sectional area greater than the cutting shaft. The distal portion includes a distal face (e.g., distal end face 396) including a partially insulated portion and an exposed portion. The insulated portions are positioned on the distal end face of the electrode, such that the insulated portions are not positioned along the cutting shaft. The exposed portion may be used to provide energy to a portion of tissue. For example, the electrode may be advanced toward tissue. With a first force applied pushing the electrode distally, the partially insulated portion may abut the portion of tissue but may prevent the exposed portion from contacting the tissue. With a second force greater than the first force applied pushing the electrode distally, the exposed portion may contact a portion of the tissue. Additionally, the distal portion of the electrode may include a length to allow a user to use the greater cross-sectional area of the distal portion to deliver energy to a portion of tissue to provide hemostasis.

The electrode may also be coupled to an actuation member, for example, in the handle or coupled to the handle, that allows a user to translate the electrode relative to the shaft. The electrode may be translatable between at least a first position in which the cutting shaft of the electrode is retracted within the shaft (FIG. 2A), and a second position in which the cutting shaft is extended beyond the shaft and exposed (FIG. 2B). In both the first and second positions, the distal portion that includes the insulated portions are extended and exposed beyond the shaft, and not retracted within the shaft.

As such, a user may position the partially insulated distal end face to abut tissue, and may apply energy via the distal end face to mark. The user may position the radial exterior of the distal portion to perform hemostasis to cauterize or coagulate tissue. The user may also position the uninsulated electrode shaft to abut or contact tissue and apply energy to cut, dissect, or ablate tissue. Different insulators with different insulation patterns may be appropriate for different medical procedures. Therefore, each electrode may be releasably coupled to distal end 16 as discussed above. Moreover, the electrode may include one or more distal outlets to provide any of the fluid flowpaths discussed above with respect to FIGS. 1A-3D.

Figure 9A:
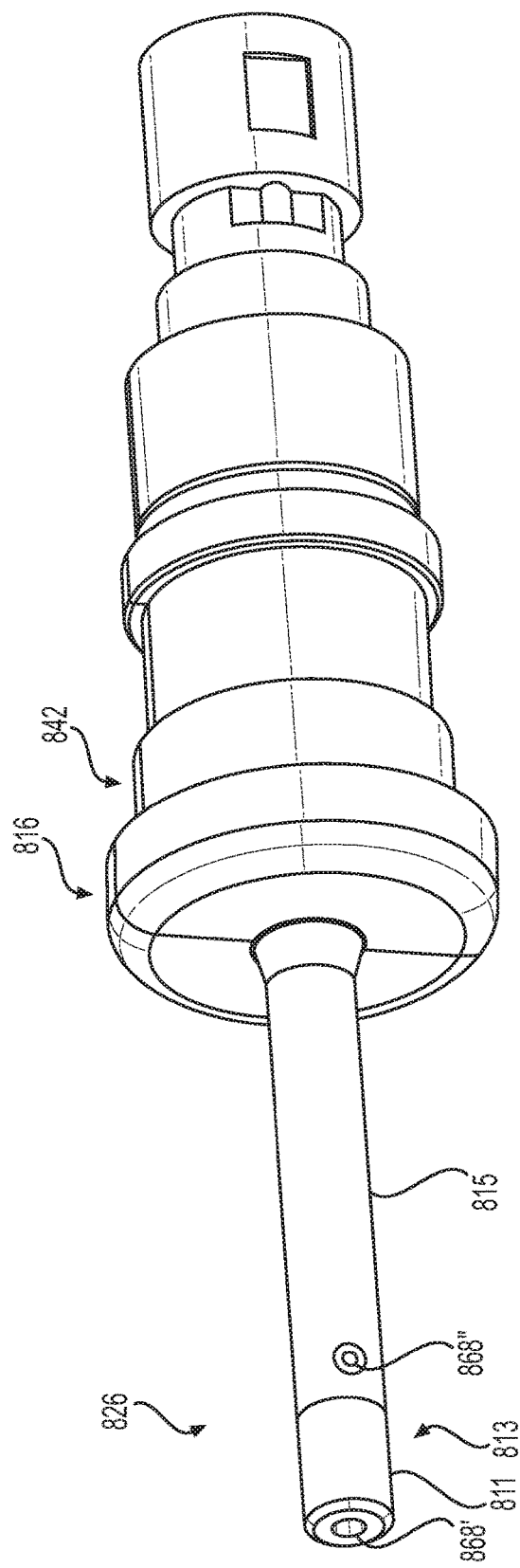
FIGS. 9A and 9B illustrate a perspective view of an exemplary distal portion of the medical device, and a cross-sectional view of the electrode of the distal portion, respectively, according to aspects of the present disclosure.
Figure 9B:
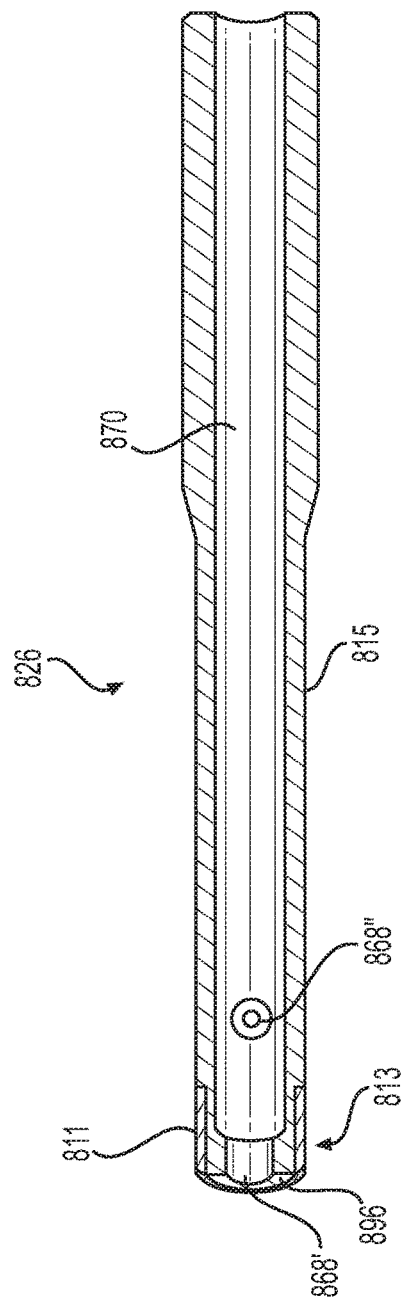

FIGS. 9A and 9B illustrate an additional example of an electrode 826. As shown, electrode 826 may include an insulator 811 on a distal end portion 813 of electrode 826. In one aspect, insulator 811 may be deposited on distal end portion 813 via ceramic deposition. Insulator 811 may be annular, having a passage therein for receiving distal end portion 813. Insulator 811 may be substantially cylindrical.

Electrode 826 may include one or more outlets 868 fluidly connected to electrode lumen 870, for example, as shown, electrode 826 may include a distal end outlet 868' and a side outlet 868". In one aspect, side outlet 868" may be smaller than distal end outlet 868' such that a majority of delivered fluid exits via distal end outlet 868', However, if distal end outlet 868' is blocked, for example, by abutting tissue, fluid may still exit electrode lumen 870 via side outlet 868". Electrode 826 may be coupled to the rest of distal end 816 and may be movable relative to an end cap 842 as discussed above. Furthermore, electrode 826 may be releasably coupled within distal end 816 with any of the mechanisms discussed above.

Electrode 826 includes an electrode body 815, which may form a cutting shaft for electrode 826. As shown in FIG. 9B, electrode 826 also includes a distal end portion 813, which has a reduced cross-sectional area (reduced relative to electrode body 815). Moreover, insulator 811 may be applied on the radial exterior of distal end portion 813 such that the diameter of distal end portion 813 and insulator 811, together, is less than or equal to the diameter of electrode body 815. In one example, the radially outer surfaces of insulator 811 and electrode body by 815 are flush. Although not shown, insulator 811 may also be provided circumferentially around distal end face 896 of electrode 826 to form an insulated distal end portion 813. In one example, the distal faces of insulator 811 and distal end portion 813 are flush. Alternatively, insulator 811 may narrow as it approaches the distal face of distal end portion 813. In either aspect, distal end portion 813 may be at least partially insulated, and electrode body 815 may be uninsulated. Accordingly, distal end portion 813 may be nonconductive to avoid stray electrical energy being directed to tissue, for example, when electrode 826 is retracted within the rest of distal end 816, but distal end portion 813 remains outside of the rest of distal end 816.

As such, electrode 826 may be coupled to an electrical element and an actuation member, as discussed above, in order to deliver energy and extend or retract electrode 826.

Electrode body 815 includes a primary axis that is coincident to a longitudinal axis of the shaft. As mentioned, distal end portion 813 includes a cross-sectional area less than or equal to the cross-sectional area of electrode body 815. Moreover, insulator 811 on distal end portion 813 does not have the longest axis of a cross-section of electrode 826, and insulator 811 does not extend over a majority of electrode 826.

Figure 10:
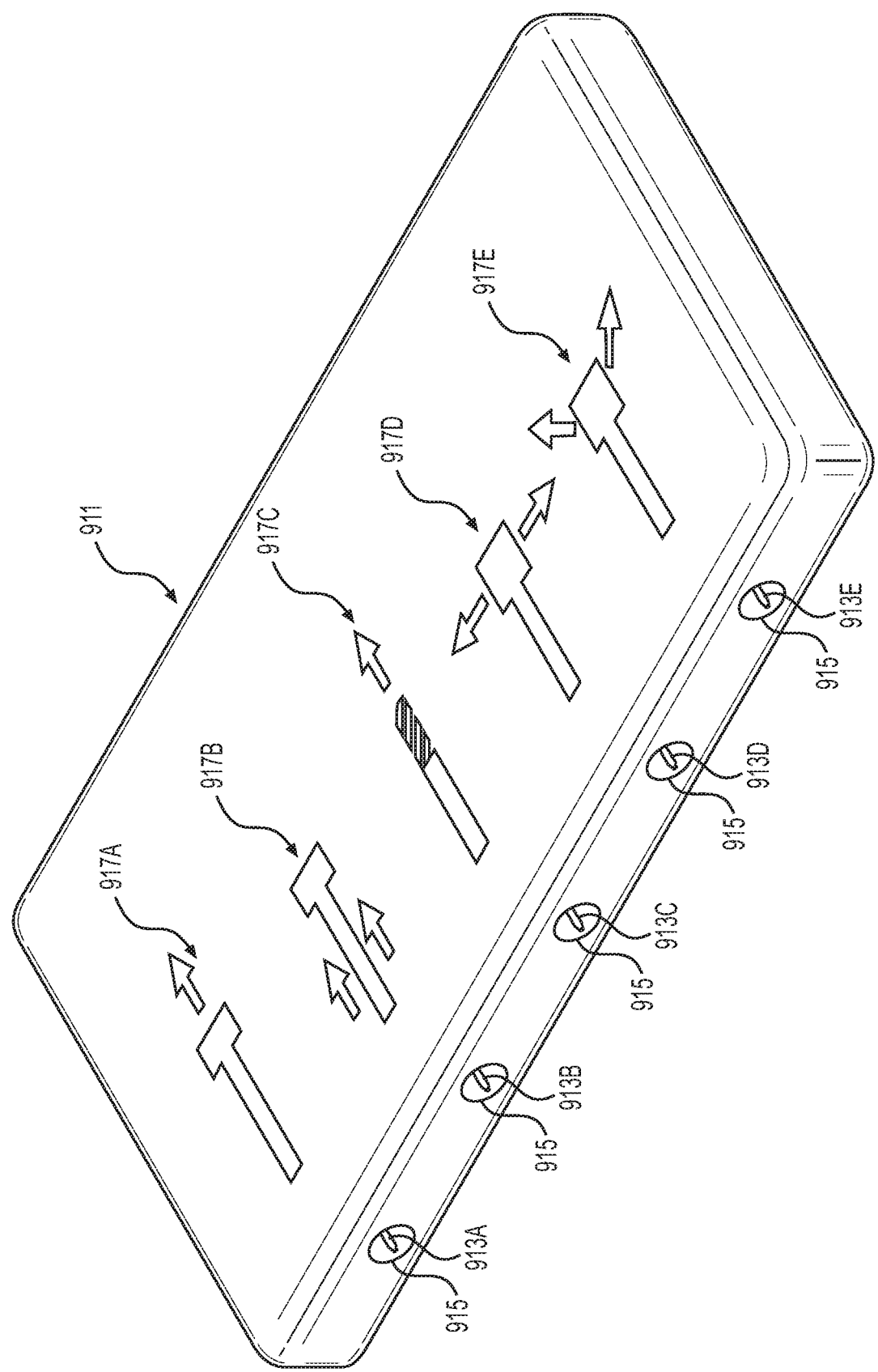
FIG. 10 illustrates a perspective view of an exemplary cartridge that may store one or more exemplary electrodes, according to further aspects of the present disclosure.

FIG. 10 illustrates an exemplary cartridge 911 with a plurality of electrodes 913A-913E stored within a plurality of openings 915. In this figure, different electrodes 913A-913E are shown within the plurality of openings 915, but it also is contemplated that any number of identical electrodes may be contained in cartridge 911. Cartridge 911 may also include one or more indications 917A-917E (e.g., text, diagrams, symbols, or the like) substantially aligned with each opening 915 to indicate the type or configuration of each of electrodes 913A-913E stored in the respective openings 915. For example, electrodes 913A-913E may include different shapes, conductive pathways, and/or fluid flowpaths, and indications 917A-917E may include a shape, silhouette, arrows, and/or an exemplary fluid flowpath of the electrodes 913A-913E stored in the respective openings 915. Although five electrodes 913A-913E and openings 915 are shown, this disclosure is not so limited. Cartridge 911 may include any number of electrodes stored in any number of respective openings, and the electrodes may include any of the configurations disclosed herein.

Figure 11A:
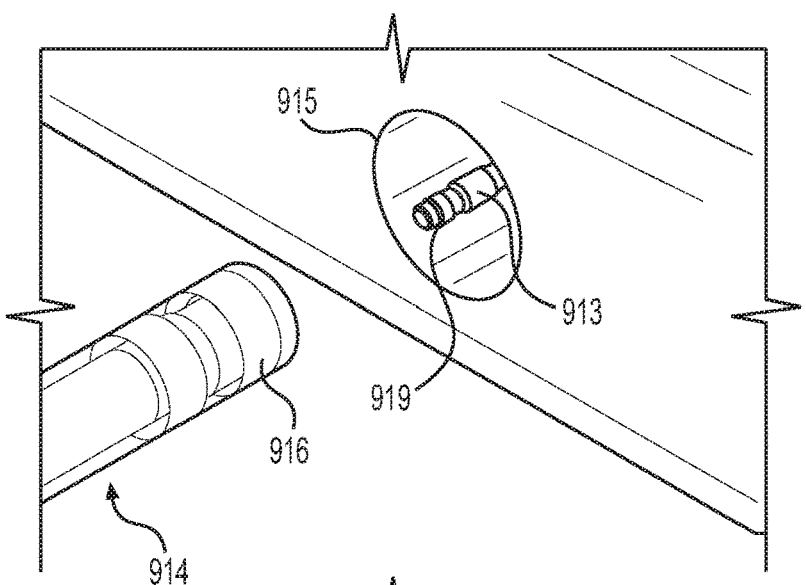
FIGS. 11A-11C illustrate exemplary steps to couple one or more exemplary electrodes stored in an exemplary cartridge, similar to the cartridge of FIG. 10, to a distal end of a medical device, according to further aspects of the present disclosure.
Figure 11B:
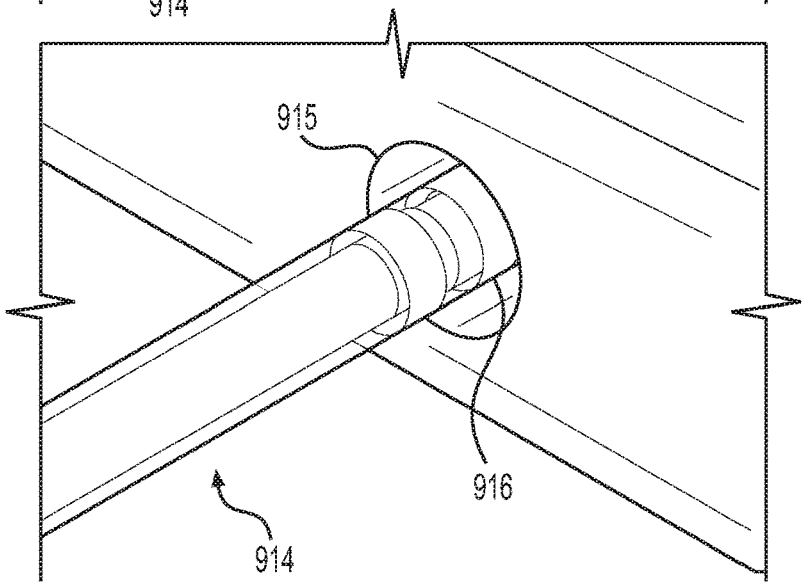
Figure 11C:
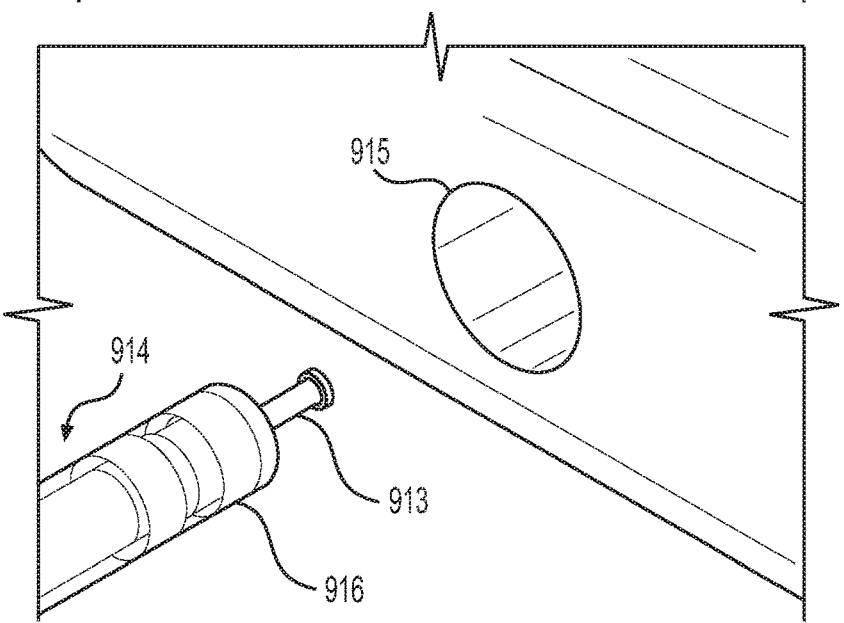

FIGS. 11A-11C illustrate steps that may be performed to couple an exemplary electrode 913 (e.g., any of electrodes 913A-913E or other electrodes disclosed herein) stored within one opening 915 of cartridge 911 to a distal end 916 of a shaft 914 of a medical device. Distal end 916 may include any of the medical device distal end aspects disclosed herein. As shown in FIG. 11A, a proximal portion 919 of electrode 913 may include one or more grooves and/or graduated portions, which may help secure the physical, electrical, and fluid connections between electrode 913 and distal end 916, as discussed above with respect to FIGS. 3A-3D, 4, 5A, and 5B. Distal end 916 may be inserted into opening 915 and may surround proximal portion 919 of electrode 913, as shown in FIG. 11B. Opening 915 may be larger than a cross-sectional area of distal end 916 to facilitate its entry into opening 915 and positioning circumferentially around at least a portion of proximal portion 919 of electrode 913, to couple electrode 913 to distal end 916. Distal end 916 may then be removed from opening 915, with electrode 913 coupled to distal end 916, as shown in FIG. 11C.

In one aspect, cartridge 911 may be configured to retain each electrode 913 in a specific position or arrangement. For example, cartridge 911 may include one or more cavities or protrusions within opening 915 that may engage with one or more portions of electrode 913. The cavities and/or protrusions within opening 915 may define a recess with a shape complementary to the shape of electrode 913. Additionally, material that forms or is within cavity 915 may be flexible to allow electrode 913 to be inserted into opening 915 and withdrawn from opening 915. In one aspect, cavity 915 and electrode 913 may be coupled via a friction fit, a snap-fit, or another type of engagement. Cartridge 911 and distal end 916 of medical device 910 may each include one or more markings, protrusions, grooves, etc. that may help a user to align electrode 913 in a proper orientation while coupling electrode 913 to the rest of distal end 916. For example, an inner wall of opening 915 may include one or more protrusions that may align with one or more grooves on an outer wall of distal end 916. In one aspect, a width of opening 915 may be slightly larger than a width of distal end 916, such that the interior walls of opening 915 may abut or engage one or more exterior portions of distal end 916, thereby ensuring that distal end 916 is properly aligned to receive electrode 913. Additionally or alternatively, the walls forming opening 915 may be tapered inwardly toward electrode 913, which may help guide distal end 915 into alignment to receive electrode 913.

The user may insert distal end 916 into opening 915 to surround at least a portion of proximal portion 919 of electrode 913 such that the coupling mechanism (e.g., one or more fastening portions 58, FIGS. 3A-3D) within distal end 916 couples electrode 913 to the rest of distal end 916. The user may then remove electrode 913 from cartridge 911 (FIG. 11C). For example, the force necessary to uncouple electrode 913 from cartridge 911 may be weaker than the force necessary to uncouple electrode 913 from the coupling mechanism within distal end 916. Although not shown, electrode 913 may be uncoupled from distal end 916 and repositioned within opening 915 in cartridge 911 for storage, cleaning, and/or later use. For example, distal end 916 may include a mechanism to uncouple electrode 913 from distal end 916, as discussed with respect to FIG. 4 above. Additionally, a different electrode 913 may then be coupled to distal end 916.

Figure 12B:
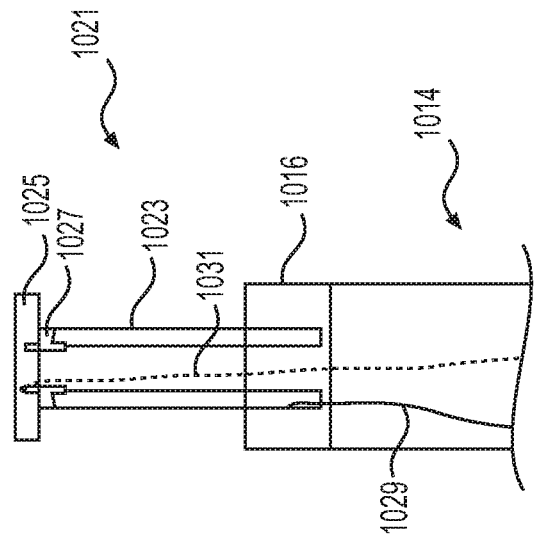
FIGS. 12A and 12B illustrate a perspective and a cross-sectional view of a further exemplary electrode, according to further aspects of the present disclosure.
Figure 12A:
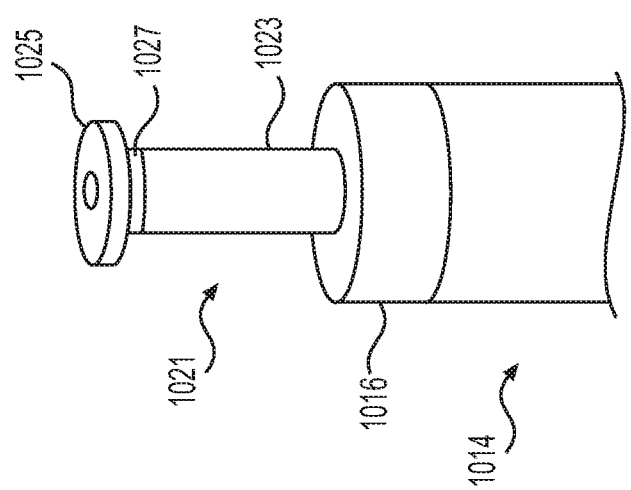

FIGS. 12A and 12B illustrate an additional exemplary electrode 1021 coupled to a distal end 1016 of a shaft 1014. Electrode 1021 may be coupled to distal end 1016 via any of the mechanisms discussed herein, and may also include any of the shapes and fluid flowpaths discussed herein. Furthermore, electrode 1021 may be used for monopolar or bipolar electrosurgery. Electrode 1021 may include at least a first conductive member 1023 and a second conductive member 1025. First conductive member 1023 and second conductive member 1025 may be electrically separated by an insulating member 1027. Insulating member 1027 may include, for example, an annular member at a distal end of first conductive member 1023 that may be received in a recess in second conductive member 1025. First conductive member 1023 may form a proximal portion of electrode 1021, and second conductive member 1025 may form a distal end portion of electrode 1021. First conductive member 1023 and second conductive member 1025 may be formed of, for example, titanium or another medically safe and conductive material. Insulating member 1027 may be formed of a ceramic, for example, aluminum oxide ($Al_2O_3$).

As shown in the cross-sectional view of FIG. 12B, electrode 1021 may include, or may receive, a first conductor 1029 and a second conductor 1031. First conductor 1029 may be connected to first conductive member 1023, and second conductor 1031 may be connected to second conductive member 1025. Each conductor may be either permanently coupled to its corresponding conductive member, for example, by soldering, adhering, and/or mechanical fixing, or may be selectively coupled, for example, by use of a plug and socket arrangement or a pin(s) and hole(s) arrangement used for mechanical and electrical coupling.

First conductor 1029 and second conductor 1031 may be electrically insulated, and may each be connected to one or more energy sources, for example, in a handle connected to shaft 1014 or in an electrosurgical generator coupled to the handle. Each of first conductive member 1023 and second conductive member 1025 may be configured to receive energy in various modes, for example, radio frequency energy in a cutting mode, a coagulation mode, etc. First conductive member 1023 and second conductive member 1025 may thus be separately energized in order to treat tissue selectively with different portions of electrode 1021.

Although FIGS. 12A and 12B illustrate electrode 1021 having first conductive member 1023 and second conductive member 1025, this disclosure is not so limited. Electrode 1021 may include three, four, five, or more separate conductive members that are separated by insulating members. Additionally, the conductive members may be longitudinally spaced on electrode 1021, may be circumferentially spaced around electrode 1021, or may be both longitudinally spaced and circumferentially spaced around electrode 1021. The respective conductive members may include respective conductors to individually energize the conductive members.

Alternatively, one conductor may be longitudinally movable within at least a portion of the electrode and controllable via the handle or another proximally located element. For example, instead of conductive members 1029 and 1031, a single moveable conductor may extend from the handle to the electrode. The conductor may be at least partially insulated such that energy is only delivered from a distal end portion of the conductor. Movement of the handle may control the position of the distal end of the single moveable conductor such that the distal end of the single moveable conductor may contact different portions of the electrode. The portions of the electrode may be insulated from the other portions of the electrodes. Therefore, a user may deliver energy through the conductor, and the longitudinal position of the conductor relative to the electrode may control which portion or portions of the electrode are energized.

Figure 13:
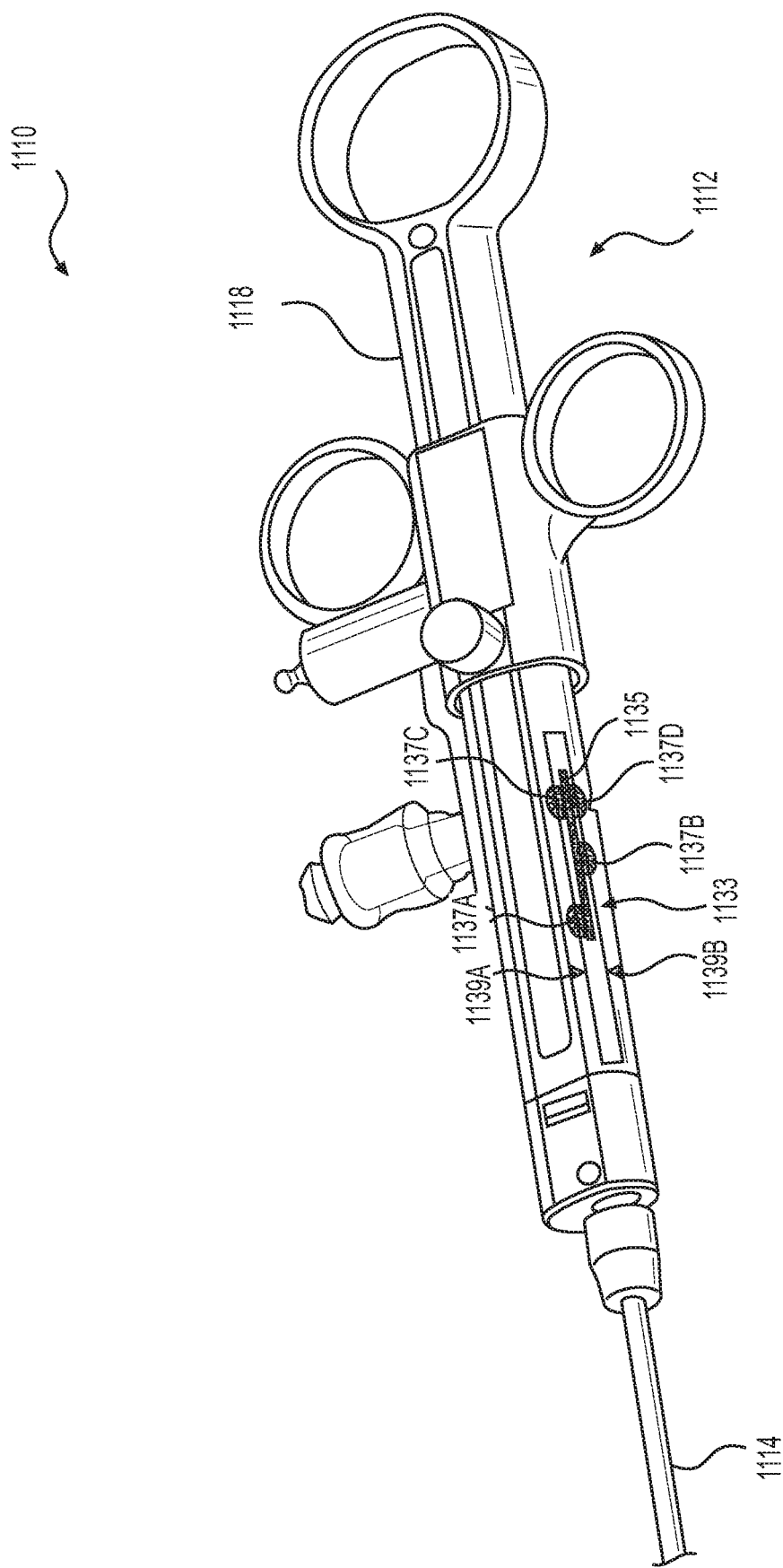
FIG. 13 illustrates a perspective view of a portion of a further exemplary medical device, according to further aspects of the present disclosure.

FIG. 13 illustrates an additional exemplary medical device 1110 with a handle 1112 and a shaft 1114. Although not shown, any of the electrodes discussed herein may be coupled to a distal end of shaft 1114. In one aspect, handle 1112 includes an activation control 1133, for example, on a main body 1118 of handle 1112. Activation control 1133 may include a plurality of buttons, switches, or other user input mechanisms that control the delivery of energy to one or more portions of the electrode coupled to shaft 1114. For example, activation control 1133 may include a slide switch 1135 that may be positioned in a plurality of positions to allow a user to control the energization of an electrode coupled to medical device 1110.

FIGS. 14A-14D illustrate various positions for activation control 1133 and the corresponding configurations of electrode 1021. For example, slide switch 1135 may be longitudinally movable (e.g., slidable) within a portion of handle 1112, and the position of slide switch 1135 corresponds to different operational states or configurations of electrode 1021. Slide switch 1135 may include one or more pads or protrusions 1137A-1137D, which may be electrically conductive pads or protrusions, for setting and/or indicating a configuration of electrode 1021. For example, slide switch 1135 may include a first protrusion 1137A on a first side of slide switch. Slide switch 1135 may include a second protrusion 1137B on a second side of slide switch 1135. Slide switch 1135 may include a third protrusion 1137C on the first side of slide switch 1135 and a fourth protrusion 1137D, aligned with third protrusion 1137C, on the second side of slide switch 1135. Each of protrusion 1137A-1137D may be electrically coupled to an electrosurgical generator (not shown) via one or more conductive wires and/or cables (not shown) running through handle 1112, and running from handle 1112 to the electrosurgical generator.

Handle 1112 may include one or more arrows 1139A and 1139B, which may be positioned on the first and second sides of slide switch 1135. Arrows 1139A and 1139B may indicate the locations of pads or protrusions on or coupled to conductors 1029 and 1031, respectively. When the pads or protrusions 1137A-1137D of slide switch 1135 contact pads or protrusions at arrows 1139A and 1139B, a circuit is completed that may direct electrosurgical energy to one or more portions of electrode 1021.

Figure 14A:
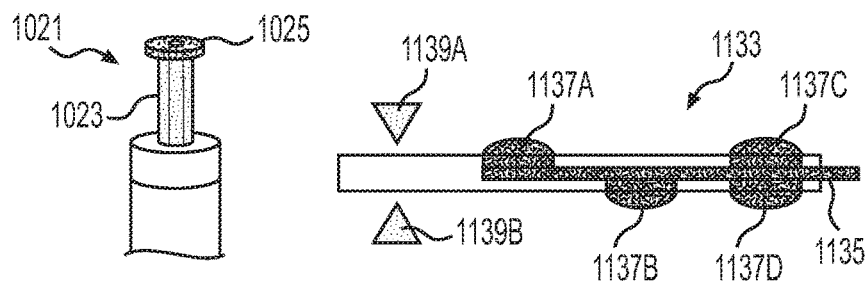
FIGS. 14A-14D illustrate various arrangements of an actuator on the medical device of FIG. 13, and the corresponding configurations of an exemplary electrode, according to further aspects of the present disclosure.

FIG. 14A illustrates activation control 1133 in an inactive configuration. For example, slide switch 1135 may be in a first position where none of protrusions 1137A-1137D are aligned with arrows 1139A and 1139B. There is a break in a circuit between an energy source (e.g., an electrosurgical generator) and electrode 1021 due to an air gap between pads or protrusions at arrows 1139A and 1139B, so current cannot flow to conductors 1029 and 1031. Accordingly, electrode 1021 may be inactive, with no energy being delivered to first conductive member 1023 or second conductive member 1025.

Figure 14B:
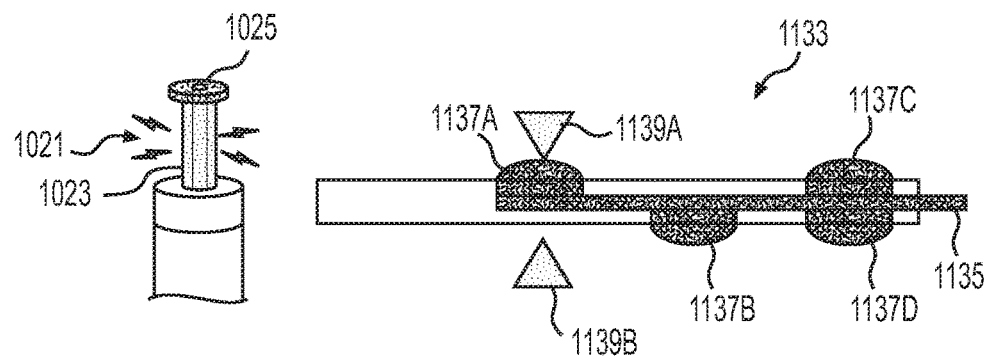

FIG. 14B illustrates activation control 1133 in a first active configuration. For example, slide switch 1135 may be in a second position, with first protrusion 1137A aligned with arrow 1139A. In this first active configuration, a circuit is completed between the energy source and electrode 1021 due to an electrical connection between protrusion 1137A and arrow 1139A. Therefore, energy may be delivered to first conductive member 1023, for example, via first conductor 1029 (FIG. 12B), such that first conductive member 1023 is energized. A circuit is not completed between one of protrusions 1137A-1137D and arrow 1139B, so no current is delivered to second conductive member 1025 via second conductor 1031.

Figure 14C:
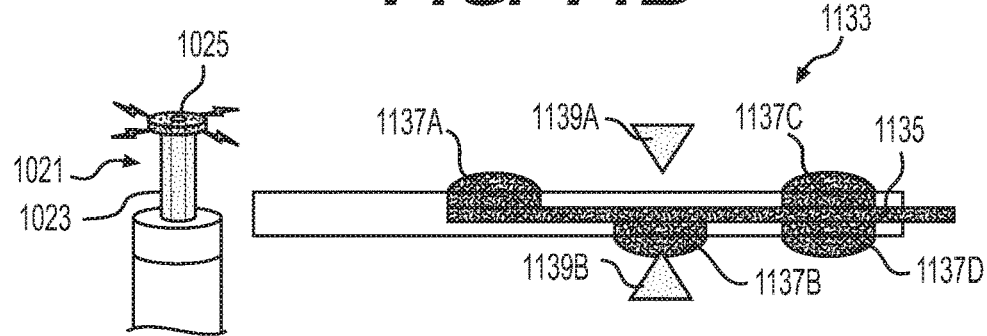

FIG. 14C illustrates activation control 1133 in a second active configuration. For example, slide switch 1135 may be in a third position, with second protrusion 1137B aligned with arrow 1139B. In this second active configuration, a circuit is completed between the energy source and electrode 1021 due to an electrical connection between protrusion 1137B and arrow 1139B. Therefore, energy may be delivered to second conductive member 1025, for example, via second conductor 1031 (FIG. 12B), such that second conductive member 1025 is energized. A circuit is not completed between one or protrusions 1137A-1137D and arrow 1139A, so no current is delivered to first conductive member 1023 via first conductor 1029.

Figure 14D:
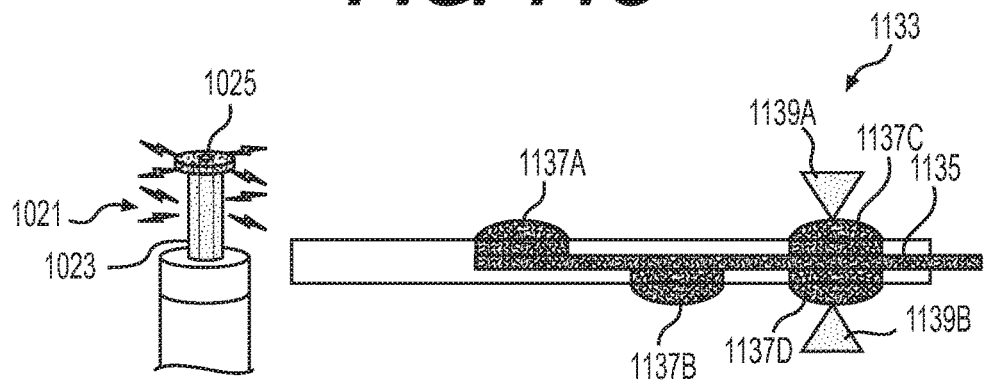

FIG. 14D illustrates activation control 1133 in a third active configuration. For example, slide switch 1135 may be a fourth position, with both third protrusion 1137C and fourth protrusion 1137D aligned with arrows 1139A and 1139B. In this third active configuration, a circuit is completed between the energy source and electrode 1021 due to an electrical connection between protrusions 1137C and 1137D and arrows 1139A and 1139B. Therefore, energy may be delivered to both first conductive member 1023 and second conductive member 1025, for example, via first conductor 1029 and second conductor 1031 (FIG. 12B), such that both first conductive member 1023 and second conductive member 1025 are energized.

Although slide switch 1135 on handle 1112 is discussed above, this disclosure is not so limited. In another aspect, medical device 1110 may include a plurality of buttons, switches, user interfaces, foot pedals, etc. that may be manipulated to selectively energize different portions of electrode 1021. For example, a first foot pedal may be depressed to energize first conductive member 1023, and a second foot pedal may be depressed to energize second conductive member 1025. A third foot pedal may be depressed to energize both first conductive member 1023 and second conductive member 1025, or simultaneously depressing both the first and second foot pedals may energize both first conductive member 1023 and second conductive member 1025. In this aspect, depressing one or more foot pedals may complete a circuit between an energy source and the respective portions of electrode 1021.

In another aspect, medical device 1110 may be coupled to a touch screen, and various user inputs on the touch screen may allow a user to control the circuitry connections, and thus energy delivery, to respective portions of electrode 1021. Furthermore, medical device 1110 may be coupled to an electrosurgical generator, and one or more switches may be positioned on the electrosurgical generator and/or on handle 1112 to control the circuitry connections and energy delivery to respective portions of electrode 1021. Conductors 1029 and 1031 may run all the way from electrode 1021 to electrosurgical generator or another energy source. Electrode 1021 may include any number of regions, and any of the control elements discussed herein may allow a user to selectively energize individual regions or groups of regions of electrode 1021. Moreover, any of the control elements may allow a user to energize different electrode regions to varying degrees (e.g., by controlling voltage, current, etc.) due to the use of separate circuitry to each region and insulation between the regions of electrode 1021.

Additionally or alternatively, slide switch 1135 may extend from handle 1112 to a distal end of device 1110. In such a configuration, pads or protrusions 1137A-1137D may be at the distal end, while a proximal portion of slide switch 1135 may extend proximally back to handle 1112, such that the user may still move pads or protrusions 1137A-1137D from handle 112. One or more arrows 1139A and 1139B also may be positioned at the distal end of device 1110. In one example, one or more arrows 1139A and 11396 may be at, or otherwise electrically coupled to, one or more portions of electrode 1021. When the pads or protrusions 1137A-1137D of slide switch 1135 contact pads or protrusions at arrows 1139A and 11396, a circuit is completed that may direct electrosurgical energy to one or more portions of electrode 1021. As noted above, the energy may be selectively directed to a portion of electrode 1021 while leaving another portion of electrode 1021 unenergized.

Energizing only the first conductive member 1023 may be useful when cutting tissue, as only energizing the shaft of electrode 1021 may help to reduce the risk of tissue perforation or other thermal damage to tissue because the blunt distal end of electrode 1021, which may be abutting tissue, is not energized. Energizing the second conductive member 1025 may be useful during an initial tissue marking, an incision, a hemostasis to increase coagulation, etc. For example, energizing the second conductive member 1025 may allow the energized distal end to deliver immediate and effective thermal treatment of tissue without the need to exchange electrode 1021 or the medical device, and may also increase the accuracy of electrode 1021. Moreover, energizing only a portion of electrode 1021 at a time may help to concentrate the delivered energy or heat in one region, which may increase the efficacy of the delivered energy or heat. As such, electrode 1021 may be used to perform various different procedures, reducing procedure time and costs.

Figure 15A:
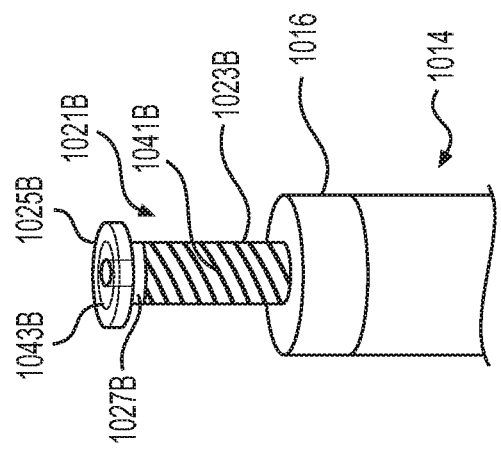
FIGS. 15A and 15B illustrate perspective views of additional electrode configurations, according to further aspects of the present disclosure.
Figure 15B:
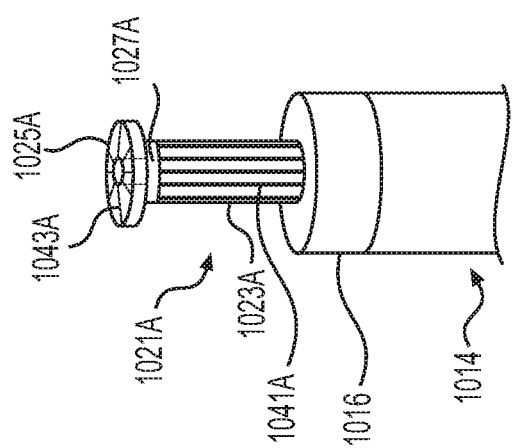

FIGS. 15A and 15B illustrate electrodes 1021A and 1021B coupled to distal end 1016 of shaft 1014, according to further aspects of this disclosure. Electrode 1021A includes a first conductive member 1023A and a second conductive member 1025A spaced apart by an insulating member 1027A. First conductive member 1023A and second conductive member 1025A may be separately energized via any of the mechanisms discussed herein to treat tissue. Additionally, first conductive member 1023A includes one or more first conductive regions 1041A. First conductive regions 1041A may be metallic deposits on a ceramic or insulating base material to form an integral first conductive member 1023A that has alternating conductive and non-conductive regions. First conductive regions 1041A may be substantially parallel lines extending along the longitudinal axis of electrode 1021A. First conductive regions 1041A may be evenly spaced. Alternatively, one side of electrode 1021A may include a denser concentration of first conductive regions 1041A than another side, providing for different energy delivering capabilities of the respective sides of electrode 1021A. First conductive regions 1041A are coupled to conductor 1029, or other similar conductors. Furthermore, all first conductive regions 1041A may be energized together, or one or more of first conductive regions 1041A may be energized individually using any of the above-described selection arrangements.

Second conductive member 1025A may include one or more second conductive regions 1043A. For example, second conductive regions 1043A may be metallic deposits on a ceramic or insulating base material to form an integral second conductive member 1025A that includes alternating conductive and non-conductive regions. Second conductive regions 1043A may be radial extensions spaced around a distal face of second conductive member 1025A. Second conductive regions 1043A are coupled to conductor 1031, or other similar conductors. Furthermore, all second conductive regions 1043A may be energized together, or one or more of second conductive regions 1043A may be energized individually using any of the above-described selection arrangements.

Electrode 1021B includes a first conductive member 1023B and a second conductive member 1025B spaced apart by an insulating member 1027B. First conductive member 1023B and second conductive member 1025B may be separately energized via any of the mechanisms discussed herein to treat tissue. Additionally, first conductive member 1023B includes one or more first conductive regions 1041B, which are coupled to conductor 1029 or similar conductors. First conductive regions 1041B may be metallic deposits on a ceramic or insulating base material to form an integral first conductive member 1023B that has alternating conductive and non-conductive regions. First conductive regions 1041B may be helical or spiral lines positioned on an exterior of first conductive member 1023B. First conductive regions 1041B may be evenly spaced. Alternatively, one portion of electrode 1021B may include a denser concentration of first conductive regions 1041B than another portion, providing for different energy delivering capabilities of the respective portions of electrode 1021B.

Furthermore, second conductive member 1025B may include one or more second conductive regions 1043B, which may be coupled to conductor 1031 or similar conductors. For example, second conductive regions 1043B may be metallic deposits on a ceramic or insulating base material to form an integral second conductive member 1025B that has alternative conductive and non-conductive regions. Second conductive regions 1043B may be circular lines spaced around a distal face of second conductive member 1025B. As such, the conductive and non-conductive regions may be annular, for example, in the form of concentric rings. As discussed above with respect to first conductive regions 1041A and second conductive regions 1043A, first conductive regions 1041B and second conductive regions 1043B may be energized together, or one or more of first conductive regions 1041B or second conductive regions 1043B may be energized individually using any of the above-described selection arrangements.

Any of the aforementioned electrodes may be selectively coupled to and uncoupled from a medical device. Similarly, once coupled to the medical device, each electrode may include separate portions that are insulated from one another, and the separate portions of the electrode may be individually energized to treat tissue.

The medical devices and methods discussed above allow a user to treat tissue by delivering electrical energy into the tissue, and delivering fluid, either simultaneously or sequentially. Additionally, the user may select one of a plurality of electrodes, including, for example, electrodes 26, 26A-26D, 126, 226, 326, 426, 526, 626, 727, 826, 913, 1021, 1021A and 1021B, to deliver the electrical energy and/or fluid, with the electrodes each having varying fluid flowpaths and/or insulators. It also is contemplated that the user may select between electrodes having similar flowpaths and/or insulation patterns, that differ in some other way. For example, electrodes having different shapes, dimensions, material properties, level(s) of use (e.g., newer versus older, or replacing worn or damaged electrodes), and/or any other characteristics. Similarly, the user may select between shafts and/or handles having different characteristics, including shapes, dimensions, material properties, level(s) of use, flexibility, operation, and/or any other characteristics.

Distal ends 16, 116, 216, 816, 916, and 1016 may allow for releasably coupling the electrodes, so a user may easily couple a first electrode to the distal end to prepare for one portion of the procedure, then remove it to prepare for another portion of the procedure. For example, a user may couple a first electrode to the distal end and deliver the distal end to an interior lumen of a subject to deliver medical therapy in a first portion of a procedure (e.g., mark, cauterize, or resect tissue). The user may then remove the distal end from the interior lumen and uncouple the first electrode from the distal end. The user may then couple a second electrode to the distal end and deliver the distal end to the lumen to deliver medical therapy for a second portion of the procedure. The second electrode may include a different fluid flowpath and/or insulation pattern than the first electrode, which may be more suitable for the second portion of the procedure than the first electrode. These steps may be repeated as many times as necessary during the procedure, using as many different types of electrodes as needed. Additionally, the user may use the same medical device 10 to deliver the various types of medical therapy by simply swapping and/or changing the electrodes coupled to distal end 16. The various fluid flowpaths and/or insulation patterns may help the user to more quickly and efficiently deliver the medical therapy, for example, cut, dissect, ablate, mark, coagulate, cauterize, or otherwise treat tissue.

Additionally or alternatively, the securing and/or removing of electrodes may be performed prior to performing a medical procedure, in preparation for performing the medical procedure. For example, the securing and/or removing of electrodes may be performed by an assembler of the medical device, and the device may then be delivered to the user for performance of a medical procedure.

Moreover, as discussed with respect to FIGS. 12-15B, a single electrode 1021, 1021A, or 1021B may allow the user to perform different tissue treatment procedures with the same electrode coupled to the distal end 1016 of the medical device. For example, a user may energize first conductive members 1023, 1023A, and 1023B to perform a cutting procedure with a reduced risk of tissue perforation because insulating members 1027, 1027A, and 1027B may help to prevent energy flowing through second conductive member 1025, 1025A, and 1025B or the distal end of electrode 1021, 1021A, and 1021B. Similarly, a user may energize second conductive members 1025, 1025A, and 1025B to perform a marking or hemostasis procedure. Lastly, a user may energize the entirety of electrodes 1021, 1021A, and 1021B for another portion of a procedure. A proximal control, for example, activation control 1133, a single moveable conductor, a slide switch, one or more actuators or foot pedals, etc., may allow the user to control the energization of electrodes 1021, 1021A, and 1021B without removing the medical device from the patient, which may help to reduce the costs and duration of the procedure, also potentially reducing the risks to the patient.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device comprising:
a shaft including a lumen configured to direct a flow of fluid through the shaft, wherein one or more arms are positioned within a distal end of the shaft, wherein the one or more arms are biased to move radially outwardly, and wherein the one or more arms are longitudinally movable within the distal end; and
an electrode,
wherein a proximal end of the electrode and the one or more arms positioned within the distal end of the shaft form a coupling configured to releasably couple the proximal end of the electrode with the distal end of the shaft, and wherein when the proximal end of the electrode is coupled to the distal end of the shaft, fluid delivered through the lumen is emitted from a distal-most portion of the electrode.

2. The medical device of claim 1, wherein each of the one or more arms includes a protrusion.

3. The medical device of claim 2, wherein each of the one or more arms further includes at least one of an angled portion at a proximal end of the protrusion and an angled portion at a distal end of the protrusion, wherein the at least one angled portion is angled relative to a central longitudinal axis of the distal end of the shaft.

4. The medical device of claim 1, wherein the electrode includes one or more receivers configured to receive the one or more arms.

5. The medical device of claim 4, wherein the one or more receivers is radially wider than a portion of the electrode distal to the one or more receivers, and/or than a portion of the electrode proximal to the one or more receivers.

6. The medical device of claim 1, further including one or more seals configured to form a fluid tight seal between the electrode and the shaft.

7. The medical device of claim 6, wherein the electrode includes an electrode lumen, wherein with the electrode coupled to the one or more arms, the one or more seals sealingly engage surfaces of the electrode and the shaft to direct fluid from the lumen to the electrode lumen of the electrode such that the lumen of the shaft and the electrode lumen form a fluid flowpath extending through the lumen of the shaft and the electrode lumen.

8. The medical device of claim 1, further including at least one biasing member configured to bias the one or more arms distally within the distal end of the shaft.

9. The medical device of claim 8, wherein the distal end of the shaft includes a central passage with an angled portion that narrows distally, and wherein the angled portion is configured to force the one or more arms radially inwardly as the one or more arms move distally within the distal end of the shaft.

10. The medical device of claim 1, wherein the electrode includes an insulator that only partially covers a distal end face of the electrode, and wherein the electrode includes an outlet in the distal end face, and wherein the insulator includes a plurality of protrusions projecting from the distal end face about the outlet.

11. The medical device of claim 1, wherein the electrode includes a first conductive member and a second conductive member, wherein the first conductive member and the second conductive member are electrically separated by an insulating member, and wherein the medical device includes a conductor that is longitudinally movable to contact and deliver energy to the first conductive member or to the second conductive member.

12. A medical device kit, comprising:
a medical device including a handle, and a shaft extending distally from the handle, wherein the shaft includes a lumen; and
a plurality of electrodes, wherein each electrode of the plurality of electrodes includes an electrode lumen configured to be fluidly connected to the lumen in the shaft,
wherein the shaft includes a distal end having a mechanism therein configured for securing one of the plurality of electrodes to the distal end of the shaft, releasing the one of the electrodes from the distal end of the shaft, and securing another of the electrodes to the distal end of the shaft, and
wherein, when a first electrode of the plurality of electrodes is secured to the distal end of the shaft, fluid delivered through the lumen of the shaft is delivered through the electrode lumen of the first electrode and out of a distal end of the first electrode such that the lumen of the shaft and the electrode lumen of the first electrode form a fluid flowpath extending through the lumen of the shaft and the electrode lumen of the first electrode.

13. The medical device kit of claim 12, wherein at least two electrodes of the plurality of electrodes differ in structure,
wherein a fluid flowpath of the medical device when one electrode of the at least two electrodes is coupled to the shaft differs from a fluid flowpath of the medical device when another electrode of the at least two electrodes is coupled to the shaft, and
wherein when the one electrode is coupled to the distal end of the shaft, fluid delivered through the lumen of the shaft is delivered through the one electrode, movement of a portion of the handle controls movement of the one electrode, and electrical energy delivered through the shaft is delivered to tissue through the one electrode.

14. The medical device kit of claim 13, wherein one or more arms are positioned within a distal end of the shaft, wherein each of the one or more arms includes a protrusion, an angled portion proximal to the protrusion, and an angled portion distal to the protrusion, wherein the one or more arms are biased to move radially outwardly, and wherein the one or more arms are longitudinally movable within the distal end of the shaft,
wherein each of the plurality of electrodes includes a receiver portion that is radially wider than a portion of the electrode distal to the receiver portion and a portion of the electrode proximal to the receiver portion, and
wherein the protrusion engages the receiver portion.

15. A medical device comprising:
a shaft including a shaft lumen configured to direct a flow of fluid through the shaft, wherein one or more arms are positioned within a distal end of the shaft, wherein the one or more arms are biased to move radially outwardly, and wherein the one or more arms are longitudinally movable within the distal end;
at least one biasing member configured to bias the arms distally within the distal end of the shaft; and
an electrode, wherein the electrode includes an electrode lumen, wherein when the electrode is coupled to the shaft, the electrode lumen is fluidly connected to the shaft lumen to form a fluid flowpath extending through the shaft lumen and the electrode lumen,
wherein a proximal end of the electrode and the one or more arms positioned within the distal end of the shaft form a coupling configured to releasably couple the proximal end of the electrode with the distal end of the shaft, and wherein when the proximal end of the electrode is coupled to the distal end of the shaft, fluid delivered through the shaft lumen flows through the electrode lumen and is emitted from a distal portion of the electrode, and
wherein the distal end of the shaft includes a central passage with an angled portion that narrows distally, and wherein the angled portion is configured to force the one or more arms radially inwardly as the one or more arms move distally within the distal end of the shaft.

16. The medical device of claim 15, wherein the electrode includes an insulator that only partially covers a distal end face of the electrode, and wherein the electrode includes an outlet in the distal end face, and wherein the insulator includes a plurality of protrusions projecting from the distal end face about the outlet.

* * * * *